US008645306B2

(12) United States Patent
Hammond

(10) Patent No.: US 8,645,306 B2
(45) Date of Patent: Feb. 4, 2014

(54) AUTOMATED CALIBRATION METHOD AND SYSTEM FOR A DIAGNOSTIC ANALYZER

(75) Inventor: Jeremy Hammond, Gorham, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 202 days.

(21) Appl. No.: 12/932,192

(22) Filed: Feb. 18, 2011

(65) Prior Publication Data

US 2012/0005150 A1    Jan. 5, 2012

Related U.S. Application Data

(60) Provisional application No. 61/398,920, filed on Jul. 2, 2010.

(51) Int. Cl.
*G06F 9/44* (2006.01)
(52) U.S. Cl.
USPC ............................................................ 706/52
(58) Field of Classification Search
None
See application file for complete search history.

(56) References Cited

U.S. PATENT DOCUMENTS

| | | | | |
|---|---|---|---|---|
| 5,410,495 | A * | 4/1995 | Ramamurthi | 702/100 |
| 5,485,550 | A * | 1/1996 | Dalton | 706/52 |
| 6,041,322 | A * | 3/2000 | Meng et al. | 706/43 |
| 6,213,958 | B1 * | 4/2001 | Winder | 600/586 |
| 6,269,276 | B1 * | 7/2001 | Akhavan et al. | 700/97 |
| 6,269,313 | B1 * | 7/2001 | Givens et al. | 702/22 |
| 6,787,361 | B1 * | 9/2004 | Klee | 436/8 |
| 6,850,874 | B1 * | 2/2005 | Higuerey et al. | 703/4 |
| 6,949,384 | B2 * | 9/2005 | Samsoondar | 436/66 |
| 6,985,749 | B2 * | 1/2006 | Bannasch et al. | 455/506 |
| 7,378,954 | B2 * | 5/2008 | Wendt | 340/539.11 |
| 7,490,073 | B1 * | 2/2009 | Qureshi et al. | 706/50 |
| 7,493,185 | B2 * | 2/2009 | Cheng et al. | 700/108 |
| 7,778,632 | B2 * | 8/2010 | Kurlander et al. | 455/418 |
| 7,788,536 | B1 * | 8/2010 | Qureshi et al. | 714/38.14 |
| 8,085,247 | B2 * | 12/2011 | Wilson | 345/173 |
| 8,099,257 | B2 * | 1/2012 | Parvin et al. | 702/179 |
| 8,170,975 | B1 * | 5/2012 | Qureshi et al. | 706/47 |
| 2002/0029130 | A1 * | 3/2002 | Eryurek et al. | 702/183 |
| 2003/0138960 | A1 * | 7/2003 | Samsoondar | 436/66 |
| 2003/0184307 | A1 * | 10/2003 | Kozlowski et al. | 324/427 |
| 2004/0068199 | A1 * | 4/2004 | Echauz et al. | 600/544 |
| 2005/0288812 | A1 * | 12/2005 | Cheng et al. | 700/109 |
| 2006/0238383 | A1 * | 10/2006 | Kimchi et al. | 340/995.1 |
| 2007/0255512 | A1 * | 11/2007 | Delenstarr et al. | 702/35 |
| 2011/0045476 | A1 * | 2/2011 | Barken et al. | 435/6 |

(Continued)

OTHER PUBLICATIONS

NCCLS, "Calibration and Quality Control of Automated Hematology Analyzers; Proposed Standard", NCCLS document H38-P, ISBN 1-56238-398-1, Apr. 1999.*

(Continued)

*Primary Examiner* — Kakali Chaki
*Assistant Examiner* — Fuming Wu
(74) *Attorney, Agent, or Firm* — Gerald T. Bodner

(57) ABSTRACT

A method to track stability and performance of diagnostic instrumentation, especially for veterinary automated hematology analyzers, applies a weighted moving averages algorithm to the diagnostic results of patient samples calculated by the analyzer. Control chart rules are used to set limits or ranges in order to determine if weighted averaged diagnostic results are within or outside of such limits or ranges. If the weighted average diagnostic results are outside of such control chart rule limits, then fuzzy logic and a gradient descent algorithm are applied to the weighted averaged diagnostic results.

17 Claims, 25 Drawing Sheets

(56) References Cited

U.S. PATENT DOCUMENTS

| | | | |
|---|---|---|---|
| 2011/0129122 A1* | 6/2011 | Stahlin et al. | 382/106 |
| 2011/0184642 A1* | 7/2011 | Rotz et al. | 701/201 |
| 2011/0276342 A1 | 11/2011 | Kazmierczak | 705/2 |
| 2012/0042214 A1* | 2/2012 | Jacobs et al. | 714/47.2 |
| 2012/0098677 A1* | 4/2012 | Geelen | 340/932.2 |
| 2012/0171672 A1* | 7/2012 | Barken et al. | 435/6.11 |

OTHER PUBLICATIONS

NCCLS, "Calibration and Quality Control of Automated Hematology Analyzers; Proposed Standard," ISBN 1-56238-398-1, 1999, USA.*

Ye, et al., "*Performance Evaluation and Planning for Patient-Based Quality Control Procedures*," Am J Clin Pathol, 2000; 113, pp. 240-248.

Westgard, et al., "*Quality Assurance*", Fundamentals of Clinical Chemistry, Third Edition, W. B. Saunders Company, 1987, pp. 249-251.

Beckman Coulter, "*XM-Exponentially Weighted Moving Average*", Beckman Coulter Technical Information Bulletin No. 9611, 2006, United States.

Flatland, et al., "*ASVCP quality assurance guidelines: control of general analytical factors in veterinary laboratories*," Vet Clin Pathol 39/3, 2010, pp. 264-277.

Cembrowski, George S., "*Thoughts on quality-control systems: a laboratorian's perspective*," Clinical Chemistry 43:5, 1997, pp. 886-892.

Westgard QC, "*QP-14: What's wrong with statistical quality control?—Westgard QC*"; http://www.westgard.com/qp-14-whats-wrong-with-statistical-quality-control.htm.

Westgard J.O., et al. "*A Multi-Rule Shewhart Chart for Quality Control in Clinical Chemistry*", Clinical Chemistry, vol. 27, No. 3, 1981, pp. 493-501.

Koch, et al. "*Selection of Medically Useful Quality-Control Procedures for Individual Tests Done in a Multitest Analytical System*", Clinical Chemistry, vol. 36, No. 2, 1990, pp. 230-233.

Lunetzky, et al. "*Performance characteristics of Bull's multirule algorithm for the quality control of multichannel hematology analyzers*", American Journal of Clinical Pathology, Nov. 1987 88(5): 634-8.

Baker, et al., "*Veterinary Hematology and Clinical Chemistry*", Ames, IA:Blackwell Publishing; 2006, pp. 17 and 84.

Simon Haykin, "*Neural Networks: A Comprehensive Foundation*", 2nd Edition, 1998, New York, NY, Macmillan College Publishing, 1998, pp. 83-85.

Yen, et al., "*Fuzzy Logic: Intelligence, Control, and Information, 1/e*", Prentice Hall Engineering/Science/Mathematics, Upper Saddle River, NJ, Prentice Hall; 1998.

VetAutoread™ Hematology Analyzer, manufactured by IDEXX Laboratories, Inc. of Westbrook, Maine, (see, www.idexx.com).

College of American Pathologists, "*Definition of Quality Assurance, Quality Control, and Quality Improvement*", Northfield, IL, www.cap.org.

Siemens Advia® 120 Hematology System, www.medical.siemens.com.

IDEXX LaserCyte® Hematology Analyzer, manufactured by IDEXX Laboratories, Inc. of Westbrook, Maine, (see, www.idexx.com).

IDEXX ProCyte Dx™ Hematology Analyzer, manufactured by IDEXX Laboratories, Inc. of Westbrook, Maine, (see, www.idexx.com).

Abbott Diagnostics, "*Cell-Dyn® 3000 Series Systems Self-Study Module*", Abbott Park, IL.

Beckman/Coulter ZBI Hematology Analyzer, Block Scientific, http://www.blockscientific.com/hematology-analyzers/beckman-coulter-zbi-hematology-analyzer.htm.

VetScan® HM5 Hematology, Abaxis, www.abaxis.com/veterinary/vetscan_hm5.html.

Patricia L. Barry, "*QC: The Levey-Jennings Control Chart*", Westgard QC, http://www.westgard.com/lesson12.htm.

Meinkoth, et al., "*Normal Hematology of the Dog*", Schalm's Veterinary Hematology, Fifth Edition, Lippincott Williams & Wilkins, NY 2000, Chapter 163, pp. 1057-1059.

Denis M. Harmening, "*Clinical Hematology and Fundamentals of Hemostasis*" Second Edition, F.A. Davis Company, Philadelphia, PA, pp. 56-58 and 532.

Heska HemaTrue™ Hematology Analyzer, Loveland, CO, http://www.heska.com/Products/Lab-Systems.aspx.

Yen, et al., "*Fuzzy Logic: Intelligence, Control, and Information, 1/e*", Prentice Hall Engineering/Science/Mathematics, Upper Saddle River, NJ, Prentice Hall; 1998.

Bull, et al., "*A Study of Various Estimators for the Derivation of Quality Control Procedures from Patient Erythrocyte Indices*", Am. J. Clin. Pathol. 1974; vol. 61:473-481.

Koepke, et al., "*Calibration and Quality Control of Automated Hematology Analyzers; Proposed Standard*", Clinical and Laboratory Standards Institute, Apr. 1999, vol. 19, No. 7.

Sysmex XT-V® Series Automated Hematology Analyzer, manufactured by Sysmex Corp. of Hyogo, Japan, wwww.sysmex.com/us/770.htm.

Sysmex XT-V® Series Automated Hematology Analyzer, manufactured by Sysmex Corp. of Hyogo, Japan, wwww.sysmex.com/us/503.htm.

Grant, et al., "The Central Limit Theorem", Statistical Quality Control, 6th Edition, p. 201, The McGraw-Hill Companies, Inc., Boston, Massachusetts, Burr Ridge, Illinois, Dubuque Iowa, Madison, Wisconsin, New York, New York, San Francisco, California, St. Louis Missouri, 1996.

\* cited by examiner

| HGB Adjustment \ RBC Adjustment | 0.91 | 0.92 | 0.93 | 0.94 | 0.95 | 0.96 | 0.97 | 0.98 | 0.99 | 1.00 | 1.01 | 1.02 |
|---|---|---|---|---|---|---|---|---|---|---|---|---|
| 0.90 | | 0.982 | 0.983 | 0.982 | 0.981 | | | | | | | 1.02 |
| 0.91 | | 0.980 | 0.981 | 0.981 | 0.981 | 0.979 | | | | | | |
| 0.92 | | | 0.978 | 0.979 | 0.979 | 0.979 | 0.978 | | | | | |
| 0.93 | | | | 0.975 | 0.976 | 0.977 | 0.977 | 0.976 | | | | |
| 0.94 | | | | | 0.973 | 0.974 | 0.975 | 0.975 | 0.974 | | | |
| 0.95 | | | | | | 0.972 | 0.973 | 0.973 | 0.973 | 0.972 | | |
| 0.96 | | | | | | | 0.970 | 0.971 | 0.971 | 0.971 | 0.970 | |
| 0.97 | | | | | | | | 0.969 | 0.970 | 0.970 | 0.969 | |
| 0.98 | | | | | | | | | 0.969 | 0.969 | 0.969 | |
| 0.99 | | | | | | | | | 0.967 | 0.968 | 0.968 | |
| 1.00 | | | | | | | | | 0.965 | 0.966 | 0.966 | |
| 1.01 | | | | | | | | | 0.963 | 0.964 | 0.964 | |

Figure 3B

AUTOMATED CALIBRATION METHOD AND SYSTEM FOR A DIAGNOSTIC ANALYZER

CROSS-REFERENCE TO RELATED APPLICATIONS

This application is related to U.S. Provisional Application Ser. No. 61/398,920, which was filed on Jul. 2, 2010, and is entitled "Automated Calibration Method and System for a Diagnostic Analyzer", the disclosure of which is hereby incorporated by reference and on which priority is hereby claimed.

BACKGROUND OF THE INVENTION

1. Field of the Invention

The present invention generally relates to diagnostic instruments for human and veterinary applications, and more specifically relates to methods and systems for calibrating such instruments.

2. Description of the Prior Art

Several studies have been published regarding patient-based quality assurance for automated analyzers. Subsets of these studies have demonstrated that patient-based results can provide information regarding analyzer performance (see, Ye J J, Ingels S C, and Parvin C A, "Performance Evaluation and Planning for Patient-Based Quality Control Procedures," Am J Clin Pathol 2000; 113: 240-248). The general focus of other investigations, and reasons for discarding the approach, was to qualify each patient result as a basis for what is reported (see, Norbert W. Tietz, Ed. Fundamentals of Clinical Chemistry, Third Ed. Philadelphia, Pa.: W.B. Saunders Company; 1987: 249-251). There is a fundamental flaw in that approach since a single patient result cannot be used to determine if it is appropriate to report. If the focus is changed slightly to monitor instrument-system performance using population data generated from aggregated patient results, then the approach has power and will provide reliable information regarding overall performance.

Weighted moving averages algorithms have been used since about 1974 for analysis of human hematology analyzer performance, starting with Bull's moving averages, sometimes referred to as X-B or $\overline{X}_B$ (see, Bull B. S., et al., "A study of various estimators for the derivation of quality control procedures from patient erythrocyte indices", Am. J. Clin. Pathol. 1974; Vol. 61:473-481). Since then, additional methodology has been introduced and implemented including exponentially weighted moving averages algorithms, sometimes referred to as EWMA, XM or $\overline{X}_M$ (see, Beckman Coulter Bulletin 9611 2006; www.beckmancoulter.com; 1-800-352-3433). In automated hematology analyzers for human samples, fixed cell controls are commonly used to determine instrument performance and calibration settings. Weighted averages provide the benefit that the analysis is performed on patient samples run on the analyzer and fill the gap between control runs, which are usually once per shift, approximately every eight hours or more frequently as recommended by organizations such as the Clinical and Laboratory Standards Institute (CLSI, Wayne, Pa.; http://www.clsi.org/; 1-877-447-1888). The use of weighted averages can provide an early warning that results may be in question even before the time to run the next control.

Diagnostic instruments have been used for decades in both the human and veterinary markets. These instruments include hematology analyzers, blood chemistry analyzers and other instruments that determine certain physiological properties of patients. In the veterinary market, the VetTest® chemistry analyzer and the VetAutoread™ automated hematology analyzer have been available since at least the 1990's. Some analyzers, like the VetAutoread™ hematology analyzer manufactured by IDEXX Laboratories, Inc. of Westbrook, Me., (see, www.idexx.com), utilize a fixed optical reference to determine instrument performance. Other analyzers, like the IDEXX LaserCyte® hematology analyzer, incorporate polymers with fixed size and index of refraction to ensure optical performance referred to as Qualibeads™. In addition, some analyzers, like the Sysmex XT-V manufactured by Sysmex Corp. of Hyogo, Japan (see, www.sysmex.com), utilize a fixed cell control material to ensure assay performance based on guidelines provided by organizations like CLSI, such as the College of American Pathologists (CAP, Northfield, Ill.; www.cap.org) and the American Society for Veterinary Clinical Pathology (ASVCP) (see, Flatland B, Freeman K P, Friedrichs K R, et al., "ASVCP quality assurance guidelines: control of general analytical factors in veterinary laboratories," Vet Clin Pathol 39/3 (2010) 264-277).

Human cells are generally utilized in the formulation of fixed-cell controls. These samples may require a specific (human) algorithm that can be very different from veterinary sample algorithms. Fundamentally, the control runs may be stable and accurate, but specific species responses may deviate due to chemical, fluidic, algorithmic, or other reasons. Patient-based methods provide species-specific analyses that can augment performance checks with fixed-cell controls and confirm that the system is performing accurately for each species.

As will be seen, the methods of the present invention also have potential applications in non-hematology systems. Chemistry analyzers commonly have optical references to verify system control. For laboratory quality results, many methods have been proposed to detect system failures with corresponding result qualification or disqualification. These methods often use analyte-specific control limits (see, Chembrowski, George S., "Thoughts on quality-control systems: a laboratorian's perspective," Clinical Chemistry 43:5, 886-892, 1997). One added benefit of patient-based quality assurance is that chemistry control products are generally based on human-expected performance, which may be significantly different with non-human samples. One criticism of patient-based quality assurance for chemistry analyzers is that, unlike many hematology parameters, chemistry results can have wide reference intervals and can have significantly wider variations in clinically ill patients. Analyte specific changes in rules or batch sizes may be required. To facilitate an understanding of the invention, the description of the preferred embodiments will be primarily directed to the hematology applications.

The veterinary market is very cost sensitive and controls are not run in the same manner as in human practices, which generally run fixed cell controls approximately at least once per 8-hour shift. Therefore, the use of weighted moving averages performed on patient samples is beneficial to veterinary applications. In addition, weighted moving averages have the additional benefit in veterinary applications that expenses are covered during normal patient runs and not in extra control materials and consumable usage. Even in analyzers with fixed cell controls, the benefit from applying a moving averages algorithm to patient samples can be great since fixed cell control material analysis loses power with increasing number of patient runs and time between control runs (see, Westgard "QP-14: What's wrong with statistical quality control? —Westgard QC"; www.westgard.com).

Bull's moving averages algorithm has been used to track patient results in automated hematology analyzers for veterinary applications (see, Sysmex XT-V; www.sysmex.com; 1-800-462-1262; Siemens Advia® 120 Hematology System; www.medical.siemens.com; 1-800-888-7436; Abbott Cell-Dyne 3700; www.abbottdiagnostics.com; (847) 937-6100)). Bull's algorithm is written in the following form (see, Bull B. S., et al. "A study of various estimators for the derivation of quality control procedures from patient erythrocyte indices", Am. J. Clin. Pathol. 1974; Vol. 61:473-481):

$$\overline{X_{B,i}} = \overline{X_{B,i-1}} + \text{sgn}\left(\sum_{j=1}^{N} \text{sgn}(X_{ji} - \overline{X_{B,i-1}})\sqrt{|X_{j,i} - \overline{X_{B,i-1}}|}\right) * \frac{\left(\sum_{j=1}^{N} \text{sgn}(X_{ji} - \overline{X_{B,i-1}})\sqrt{|X_{j,i} - \overline{X_{B,i-1}}|}\right)^2}{N}$$ (Eq. 1)

Generally, Bull's algorithm groups 20 consecutive patient results into a single Bull batch based on Equation 1. The following logic flow describes the steps used in the above equation to determine Bull batch values:

1. Determine the average of the first N=20 samples; this is the first Bull batch;
2. For each of the next N=20 samples, calculate the absolute difference between each patient result and the previous Bull batch;
3. Sum all of the values from step (2), maintaining the sign of the difference within the sum;
4. Square the result from Step (3) and divide by N;
5. Add the result from Step (4) to the previous Bull batch to define the current Bull batch; and
6. Repeat Steps (2)-(5) for all remaining Bull batch calculations.

A graphical representation/flow chart of the steps described above in applying Bull's algorithm to generate summary batches from individual patient results is shown in FIG. 1A.

There are many benefits of utilizing Bull batches to summarize patient samples into a control chart, which is displayed on the analyzer so that the clinician may determine if the analyzer needs to be re-calibrated, even during the period between fixed cell control tests. The Bull weighted moving averages algorithm provides a means to reduce the impact of single sample variations on batch results. Also, utilizing the analysis for red cell indices, that is, RBC (red blood cells), MCV (mean corpuscular volume), HGB (hemoglobin), HCT (hematocrit), MCH (mean corpuscular hemoglobin), and MCHC (mean corpuscular hemoglobin concentration), has additional benefit since several of the parameters (MCV, MCH, and MCHC) have tight normal variations, within species, that can provide additional information with respect to result accuracy. Many concerns related to specialty practices running multiple sick patients and oncology patients can be mitigated since there are few clinical conditions that drive significant variation in MCV, MCH, and MCHC for a population of patients.

By removing runs that have clinical flags or impossible responses (such as a zero occurring from a short sample), Batch results will provide easily charted results that are not heavily weighted by outlier results that are due to patient response, sample handling, analyzer variation or the like.

More specifically, results must be qualified prior to inclusion in the batch analysis. Repeat runs on a particular patient within a batch are removed. Runs that have clinical or analyzer flags are removed. Runs with impossible responses, such as those stemming from a gross instrument error like a short sample, are removed. Batch results provide easily charted values that are not heavily weighted by outlier results due to patient response, sample handling, or analyzer variation. Outlier runs, defined as patient results that report significantly different than the normally measured population on that analyzer either due to patient response or system malfunction (FIG. 1(a)), have no significant impact on batches. Due to flagging and other internal checks, these results are often not reported to the user. The 20 sample-average batch results track very well with patient population results.

FIG. 1 shows a representation of MCHC results, both as raw patient results and as Bull batches. As stated above, outlier runs, shown in FIG. 1(a), are shown to have limited impact on Bull batches. In addition, FIG. 1(b) shows the same data set from FIG. 1(a), zooming in on the results without outliers and identifying that the Bull batches track very well with patient population results.

More specifically, FIG. 1 is a set of graphs of MCHC equine patient results with associated Bull batches for an automated hematology analyzer. FIG. 1(a), with all data included, shows little impact from outliers on Bull batches (20 runs per batch). FIG. 1(b) is a zoom in on largest population of instrument response taken from FIG. 1(a) showing that the Bull batches track the population variation.

Control chart rules are in place in many conventional hematology analyzers to provide feedback when the Bull batches show a trend or bias outside of limits. Standard Westgard Rules have been used in multiple applications of weighted moving averages in chemistry and hematology automated analyzers (see, Westgard J. O., et al. "A Multi-Rule Shewhart Chart for Quality Control in Clinical Chemistry", Clin. Chem. 27/3, 493-501, 1981; Koch D. D. "Selection of Medically Useful Quality-Control Procedures for Individual Tests Done in a Multitest Analytical System", Clin. Chem., Vol. 36, No 2: 230-233, 1990; Lunetzky E S Cembrowski G S, "Performance characteristics of Bull's multirule algorithm for the quality control of multichannel hematology analyzers", American Journal of Clinical Pathology, 1987 Nov. 88(5):634-8. Rules implemented on Bull batches can have higher power than the same number of patient results, since each Bull batch corresponds to 20 patient runs. The act of grouping runs into batches that also include prior batch values provides a smoothing effect, so a rule that may otherwise require 10 points can now be utilized with far fewer points.

In most if not all conventional hematology analyzers, whether for human or veterinary applications, it is the clinician who must manually compare the control charts depicted as graphs displayed on the analyzer to determine whether the analyzer is out of calibration and needs adjustment of one of its parameters, such as optical gain, for example. This applies whether or not the control charts are derived from periodically run fixed cell controls, or from a weighted moving average applied to patient samples. To the knowledge of the inventor, no automated system or method is employed in either human hematology analyzers or veterinary hematology analyzers which monitors the performance of such analyzers based on patient samples and through feedback adjusts the parameters of the analyzer in real time to maintain the analyzer within its calibration specifications.

OBJECTS AND SUMMARY OF THE INVENTION

It is an object of the present invention to provide an automated system and method for calibrating a diagnostic instrument, such as a hematology analyzer, in real time.

It is another object of the present invention to provide a system and method for calibrating a hematology analyzer which automatically employ a weighted moving averages algorithm on patient samples to monitor the performance of the analyzer and through feedback adjust the parameters of the analyzer to maintain the analyzer within its calibration specifications.

It is yet another object of the present invention to provide a system and method for automatically calibrating a human or veterinary diagnostic instrument, such as a hematology analyzer, based on patient samples using a weighted moving averages algorithm, fuzzy logic and a gradient descent algorithm.

It is a further object of the present invention to provide an automated system and method for calibrating a diagnostic analyzer which overcome the inherent disadvantages of known analyzer calibration systems and methods.

In accordance with one form of the present invention, a system and method for automated, real time calibration of a diagnostic instrument, which includes but is not limited to a hematology analyzer, such as the aforementioned LaserCyte® analyzer or the ProCyte Dx® analyzer, the first being manufactured by IDEXX Laboratories, Inc. and the second being manufactured by Sysmex Corporation, or a dry reagent test slide chemical analyzer, such as the Catalyst DX® analyzer, also manufactured by IDEXX, to name a few (collectively referred to herein as "diagnostic analyzers"), used for veterinary or human applications, receive the diagnostic (e.g., hematology) results of patient samples calculated by the analyzer using the analyzer's pre-set parameters (such as optical gain, for example), and apply a weighted moving averages algorithm to the patient sample diagnostic results to obtain weighted averaged diagnostic results. Then, Westgard Rules or any other SPC control chart rules are applied to the weighted averaged diagnostic results. The control chart rules (or more preferably, Westgard Rules) create limits or ranges which are used to test the extent to which the weighted averaged diagnostic results reside within such limits or ranges. Thus, the weighted averaged diagnostic results are compared with such control chart rule limits or ranges. If the weighted averaged diagnostic results fall within the control chart rule limits or ranges, then no multiplying factor is applied to the patient sample diagnostic results calculated by the analyzer using its pre-set parameters (e.g., optical gain).

However, should the weighted averaged diagnostic results fall outside of the control chart rules limits or ranges during such a comparison, then the method and system of the present invention apply fuzzy logic and a gradient descent algorithm to the weighted averaged diagnostic results to obtain adjusted diagnostic results of the patient samples which are now within the acceptable limits or ranges of the control chart rules. Such adjusted diagnostic results are read out or displayed by the analyzer and represent a more accurate calculation of the patient sample diagnostic results.

Also, one or more multiplying factors are derived from the application of the fuzzy logic and the gradient descent algorithm to the weighted averaged diagnostic results. The multiplying factor (or factors) is used in modifying the calculations performed by the analyzer with its pre-set parameters to correct the results of such calculations without the need to actually change the analyzer's pre-set parameters stored in the analyzer's memory. Thus, for example, by applying the derived multiplying factor, the overall gain to the analyzer's optical system may be effectively adjusted from 1.03 to 1.04 to more accurately provide patient sample diagnostic results read out or displayed by the analyzer.

The calibration method is preferably applied each time the diagnostic analyzer generates patient sample results so that the calculated results may be automatically adjusted in real time, and the multiplying factor (which is applied to the analyzer's pre-set parameters) may be continually changed as is required, in order to provide more accurate patient readings.

In a more preferred embodiment of the present invention, the weighted moving averages algorithm applied to the patient samples is Bull's algorithm. Furthermore, in another preferred form of the invention, the control chart rules which are applied to the weighted moving averages algorithm are Westgard Rules, and red cell index targets and ranges are derived for the application of the Westgard Rules. In use, particularly when running human analyzers, the user could be alerted that an adjustment is likely needed. The user can then allow the adjustment and follow-up with a control fluid to ensure the adjustment was proper, i.e. before running additional samples. For veterinary applications, adjustments can be made automatically. Also, in the veterinary field, targets and ranges are typically species specific, e.g. dogs, cats, horses.

A system which implements the automated calibration method of the present invention can be realized by software, or more precisely, an application program, or by firmware or hardware. The system may include a memory, such an EEPROM (electronically erasable programmable read only memory) in which are stored the weighted moving averages algorithm, the control chart rules, the fuzzy logic, the gradient descent algorithm and the multiplying factor. Memories or storage devices are also provided for storing the unadjusted diagnostic results of patient samples calculated by the analyzer using the pre-set parameters (e.g., optical gain) of the analyzer, the weighted averaged diagnostic results resulting from the application of the weighted moving averages algorithm, and the adjusted or corrected diagnostic patient sample results resulting from the application of the fuzzy logic and the gradient descent algorithm. A microprocessor, microcontroller or CPU may be employed to carry out the application of the weighted moving averages algorithm, the control chart rules, the fuzzy logic and the gradient descent algorithm to the patient data, or make any comparisons to determine if the weighted averaged diagnostic results are within the control chart rule limits or ranges, and derive the multiplying factor to be applied to the analyzer's pre-set parameters. Of course, it should be realized that such structure (e.g., memories, microprocessor and the like) may already exist within the analyzer, and such structure may be conveniently utilized in performing the functions of the automated calibration method of the present invention.

These and other objects, features and advantages of the present invention will be apparent from the following detailed description of illustrative embodiments thereof, which is to be read in connection with the accompanying drawings.

BRIEF DESCRIPTION OF THE DRAWINGS

FIG. 1 is a set of graphs plotting MCHC (mean corpuscular hemoglobin concentration) equine patient sample results against instrument run numbers with associated Bull batches for an automated diagnostic analyzer, where FIG. 1(a) includes all data and shows little impact from outliers on all batches (20 runs per batch)

FIG. 3B is a chart of a 2-d gradient descent fuzzy correlation function based on effective results of adjustments on RBC, MCV and HGB with correlated calculated parameters HCT, MCH and MCHC in accordance with the method of the present invention.

FIG. 5 is a set of graphs plotting Bull batches calculated from the diagnostic analyzer dataset used in FIG. 4 and corrected values based on Westgard Rules triggering gradient descent and fuzzy logic adjustments, in accordance with the present invention. The gray points denoted in the figures represent raw patient Bull batches, while the black points represent Bull batches after adjustment logic was implemented. Bull targets and reference ranges are included, where appropriate.

FIG. 6 is a graph plotting PCV (packed cell volume) (as a percentage) against HCT (as a percentage) after corrections to the patient sample results are implemented in accordance with the present invention. The ordinate of the graph of FIG. 6 represents PCV percentage values, while the abscissa of the graph represents HCT as percentage values. The upper limit (UL) and lower limit (LL), as well as a line where PCV equals HCT, are shown in FIG. 6. Multiple different instruments where included in the analysis from which FIG. 6 is derived.

DETAILED DESCRIPTION OF THE PREFERRED EMBODIMENTS

Figure 1A:
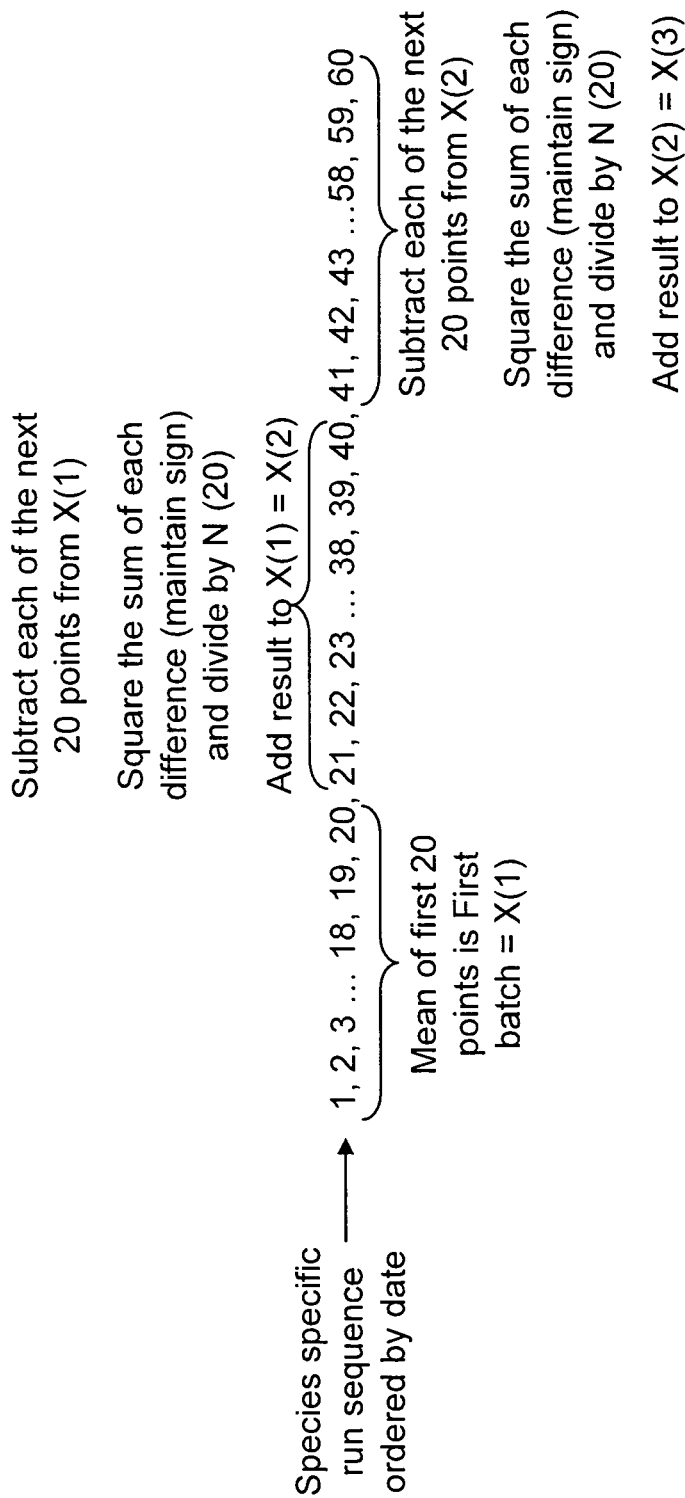
FIG. 1A is a graphical representation/flow chart of steps used in applying Bull's algorithm to generate summary batches from individual patient results.
Figure 1A:
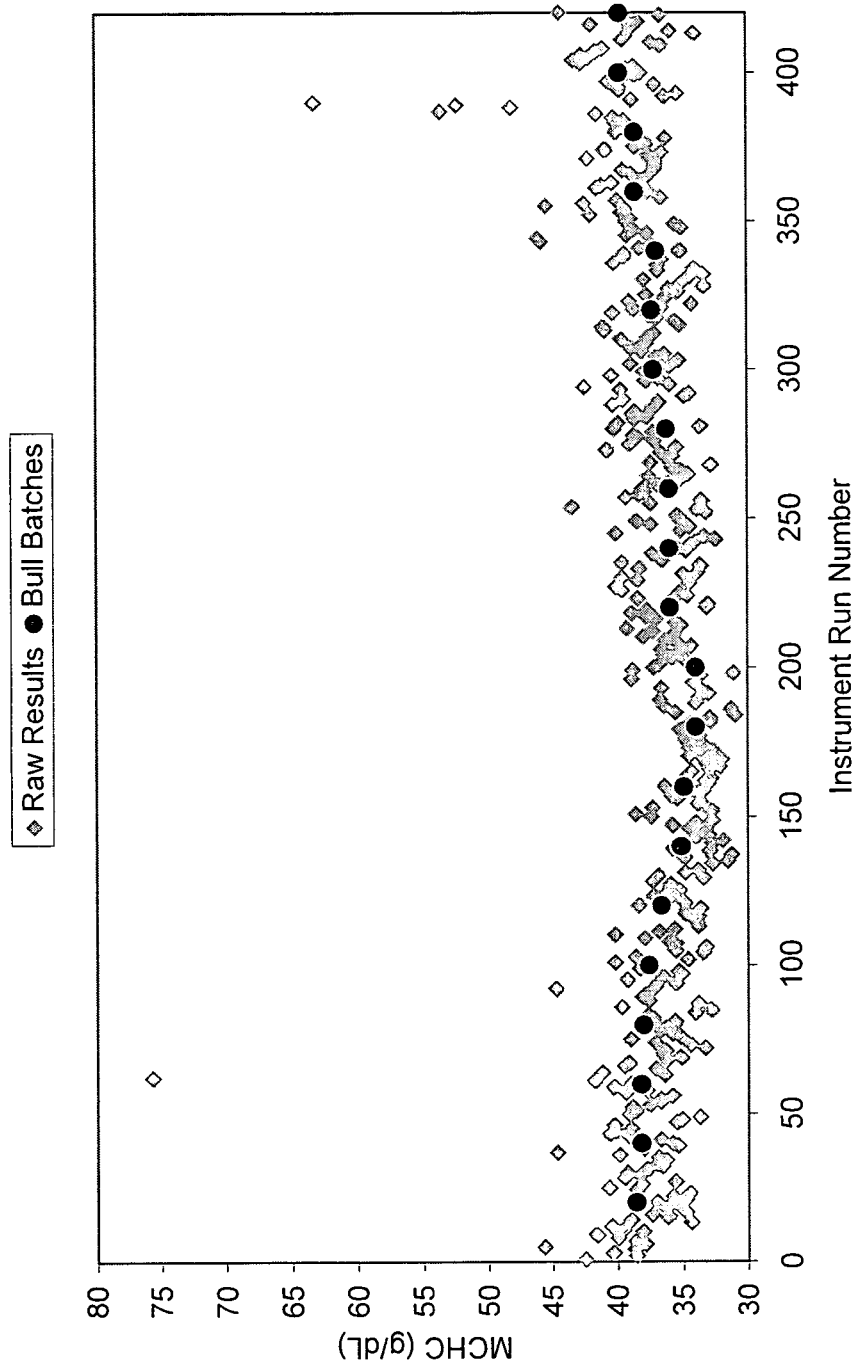
Figure 1B:
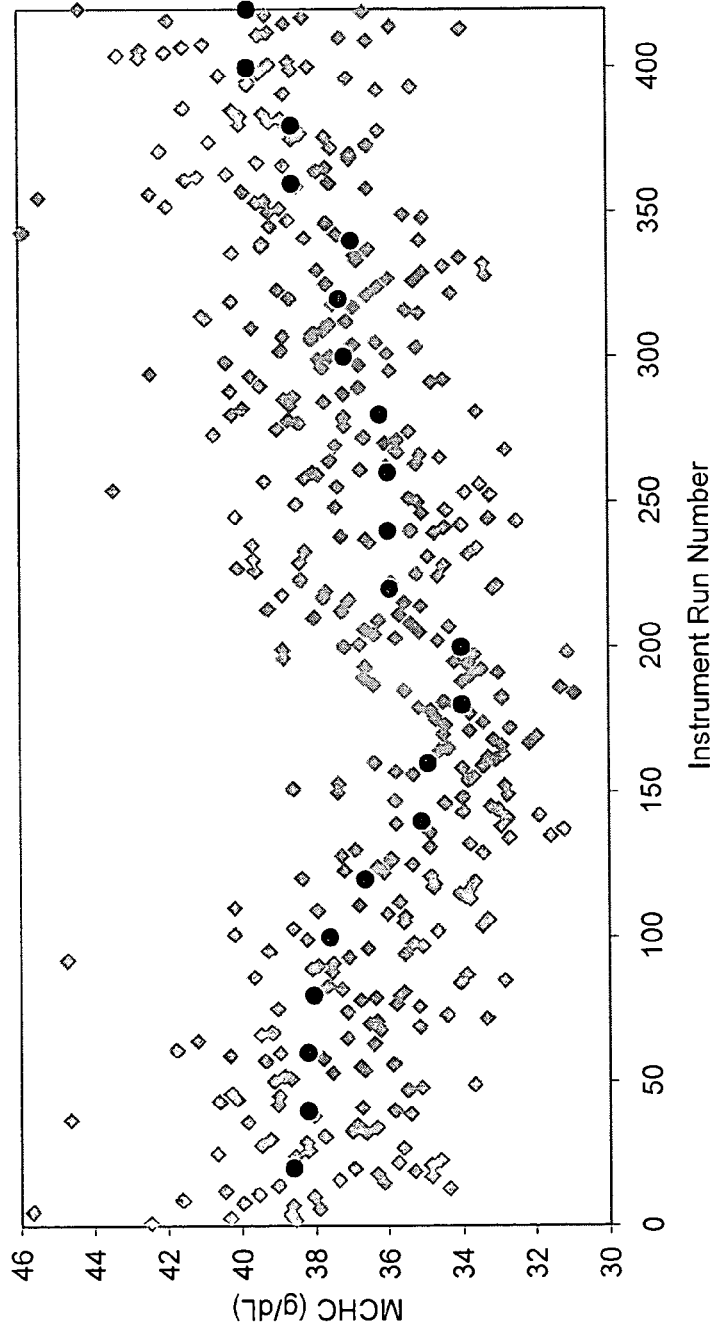
FIG. 1(b) shows a zoom in on the largest population of instrument response from FIG. 1(a) and shows that the Bull batches track the population variation.

A preferred form of the method of the present invention, and system implementing the method, will now be described. In accordance with one form of the present invention, an automated method for calibrating in real time a diagnostic analyzer, such as a hematology analyzer, preferably includes the steps of receiving the diagnostic (e.g., hematology) results of patient samples calculated by the analyzer using the analyzer's pre-set parameters (such as optical gain, for example), and applying a weighted moving averages algorithm to the patient sample diagnostic results to obtain weighted averaged diagnostic results. The method further includes the steps of applying control chart rules to the weighted averaged diagnostic results, and creating from the control chart rules limits or ranges which are used to test the extent to which the weighted averaged diagnostic results reside within such limits or ranges. The method further includes the steps of comparing the weighted averaged diagnostic results with such control chart rule limits or ranges. If the weighted averaged diagnostic results fall within the control chart rule limits or ranges, then no multiplying factor is applied to the patient sample diagnostic results calculated by the analyzer using its pre-set parameters (e.g., optical gain).

However, should the weighted averaged diagnostic results fall outside of the control chart rule limits or ranges during such a comparison, then the method of the present invention further includes the step of applying fuzzy logic and a gradient descent algorithm to the weighted averaged diagnostic results to obtain adjusted diagnostic results of the patient samples which are now within the acceptable limits or ranges of the control chart rules. Such adjusted diagnostic results are read out or displayed by the analyzer and represent a more accurate calculation of the patient sample diagnostic results.

Furthermore, the automated calibration method includes the steps of deriving from the application of the fuzzy logic and the gradient descent algorithm to the weighted averaged diagnostic results one or more multiplying factors, and modifying the calculations performed by the analyzer with its pre-set parameters by the multiplying factor (or factors) to correct the results of such calculations without the need to actually change the analyzer's pre-set parameters stored in the analyzer's memory. Thus, for example, by applying the derived multiplying factor, the overall gain to the analyzer's optical system may be effectively adjusted from 1.03 to 1.04 to more accurately provide patient sample diagnostic results read out or displayed by the analyzer.

The calibration method is preferably applied each time the diagnostic analyzer generates patient sample results so that the calculated results may be adjusted in real time, and the multiplying factor (which is applied to the analyzer's pre-set parameters) may be continually changed as is required, in order to provide more accurate patient readings.

In a more preferred embodiment of the present invention, the weighted moving averages algorithm applied to the patient samples is Bull's algorithm. Furthermore, in another preferred form of the invention, the control chart rules which are applied to the weighted moving averages algorithm are Westgard Rules, and red cell index targets and ranges are derived for the application of the Westgard Rules. In use, particularly when running human analyzers, the user could be alerted that an adjustment is likely needed. The user can then allow the adjustment and follow-up with a control fluid to ensure the adjustment was proper, i.e. before running additional samples. For veterinary applications, adjustments can be made automatically. Also, for veterinary applications, red cell targets and ranges are derived for certain selected species of animals. More specifically, in the veterinary field, targets and ranges are typically species specific, e.g. dogs, cats, horses.

In accordance with one form of the present invention, control chart rules are implemented by the method to provide feedback when the Bull batches show a trend or bias outside of certain limits. As stated previously, the system and method of the present invention preferably employ Westgard Rules.

The method of the present invention preferably selects two rules for control charts using Bull batches. The first is identified as $2_{SL}$, where a control error is generated when two consecutive batches exceed the same specified limit. The second is identified as $4_{\bar{x}}$, where a control error is generated when four consecutive batches fall on one side of the target.

In veterinary applications, in particular, limits have been defined for MCV, MCH, and MCHC based on independent studies of species specific variation. Preferred specific values used, by species, are listed in Table 1A, shown below:

TABLE 1A

Red Cell Index Targets and Ranges for Westgard Rules

| Red Cell Index | Canine Target | Canine Range | Feline Target | Feline Range | Equine Target | Equine Range |
|---|---|---|---|---|---|---|
| MCV (fl) | 70 | 2 | 48 | 2 | 44 | 2 |
| MCH (g) | 23.3 | 2 | 16 | 2 | 14.7 | 2 |
| MCHC (g/dl) | 33.3 | 1.5 | 33.3 | 1.5 | 33.3 | 1.5 |

Table 1B presents the same data shown in Table 1A, except that intervals are shown in Table 1B instead of the ranges shown in Table 1A.

TABLE 1B

Red Cell Index Targets and Intervals for Control Chart Rules.

| Red Cell Index | Canine Target | Canine Interval | Feline Target | Feline Interval | Equine Target | Equine Interval |
|---|---|---|---|---|---|---|
| MCV (fL) | 70 | 68-72 | 48 | 46-50 | 44 | 42-46 |
| MCH (pg) | 23.3 | 21.3-25.3 | 16 | 14-18 | 14.7 | 12.7-16.7 |
| MCHC (g/dL) | 33.3 | 31.8-34.8 | 33.3 | 31.8-34.8 | 33.3 | 31.8-34.8 |

Specifically, MCHC is useful for measuring instrument performance since clinical conditions resulting in low MCHC values are relatively uncommon. Additionally, in vivo hemolysis increases in MCHC associated with intravascular hemolytic disease are relatively uncommon. In vitro hemolysis due to poor sample handling may be problematic; therefore, proper sample handling techniques must be followed. Lipemia and conditions causing Heinz body formation may be problematic also resulting in false increased hemoglobin measurement and resulting increased MCHC calculation (see, Thrall M A, Baker D C, Campbell T, et al., "Veterinary Hematology and Clinical Chemistry," Ames, Iowa: Blackwell Publishing; 2006).

The relationships between RBC (M/ul), MCV (fl), and HGB (g/dl) to the calculated parameters HCT (%), MCH (g), and MCHC (g) provide the basis for adjustments to the measured parameters in accordance with the method of the present invention. The relationships between HCT, MCH, and MCHC are displayed in Equations 2, 3, and 4, respectively, as shown below:

$$HCT = \frac{RBC * MCV}{10} \quad \text{(Eq. 2)}$$

$$MCH = 10 * \frac{HGB}{RBC} \quad \text{(Eq. 3)}$$

$$MCHC = 1000 * \frac{HGB}{RBC * MCV} \quad \text{(Eq. 4)}$$

Since MCV, MCH, and MCHC have targets and ranges, Equations 2 through 4 provide three equations with three unknowns (RBC, HGB, and HCT). Since MCH and MCHC are not independent equations (MCH is related to MCHC directly by MCV), there is now only two equations (Eq. 2 and 4) with three unknowns (RBC, HGB, and HCT). In accordance with the method of the present invention, a gradient descent algorithm (see, Haykin, Simon, "Neural Networks: A Comprehensive Foundation" (2nd Edition), 1998) and fuzzy logic (see, Yen, John and Reza Langari, "Fuzzy Logic: Intelligence, Control, and Information", 1998) are employed and will provide optimized RBC and HGB adjustments to pair with MCV adjustments (based on the MCV target) for HCT, MCH, and MCHC in accordance with fuzzy logic principles. A simple confirmation of results can be made by splitting a patient sample and performing a spun HCT (PCV) to confirm results.

More specifically, fuzzy logic algorithms are preferably utilized in the present invention, in addition to the system of equations above, to incorporate expert human decisions. Fuzzy logic provides an improvement over traditional logic programming, where case statements (if-then) are used to determine if an expression is true or false, with appropriate actions for either condition. Fuzzy logic will assign levels of correctness; for example, a value can be 30% or 70% true. An example of an application of fuzzy logic is determining if a person's age of 35 is old or young, which depends on the point of origin for the comparison. Fuzzy logic attempts to incorporate expert logic within context. To implement fuzzy logic in the present invention, a software-implemented expert system in the analysis of hematology results and comparison with split references will describe each logical input that defines action based on the data. These logical inputs are then translated into fuzzy relationships that the software tool will use moving forward. The logical inputs are essentially training sets for the fuzzy logic algorithm that are then implemented and compared with new test cases.

In accordance with the present invention, fuzzy logic is implemented using targets, ranges, and Equations 2-4, and this combination will provide a basis for determining analyzer system adjustments that will positively impact the analyzer's calculated results. An example of how the automated method and system may be used to correct in real time patient sample results determined by a diagnostic analyzer, such as a hematology analyzer, and calibrate the analyzer, will now be described. In this example, a hematology instrument is biased, and FIGS. 4(*a*)-4(*f*) show the results of the instrument's bias in the determinations of RBC, MCV, HGB, HCT, MCH, and MCHC. Target ranges are included for MCV, MCH, and MCHC following Table 1. Targets are partially obstructed on the MCH and MCHC graphs due to the density of points overlapping the ranges.

Figure 2:
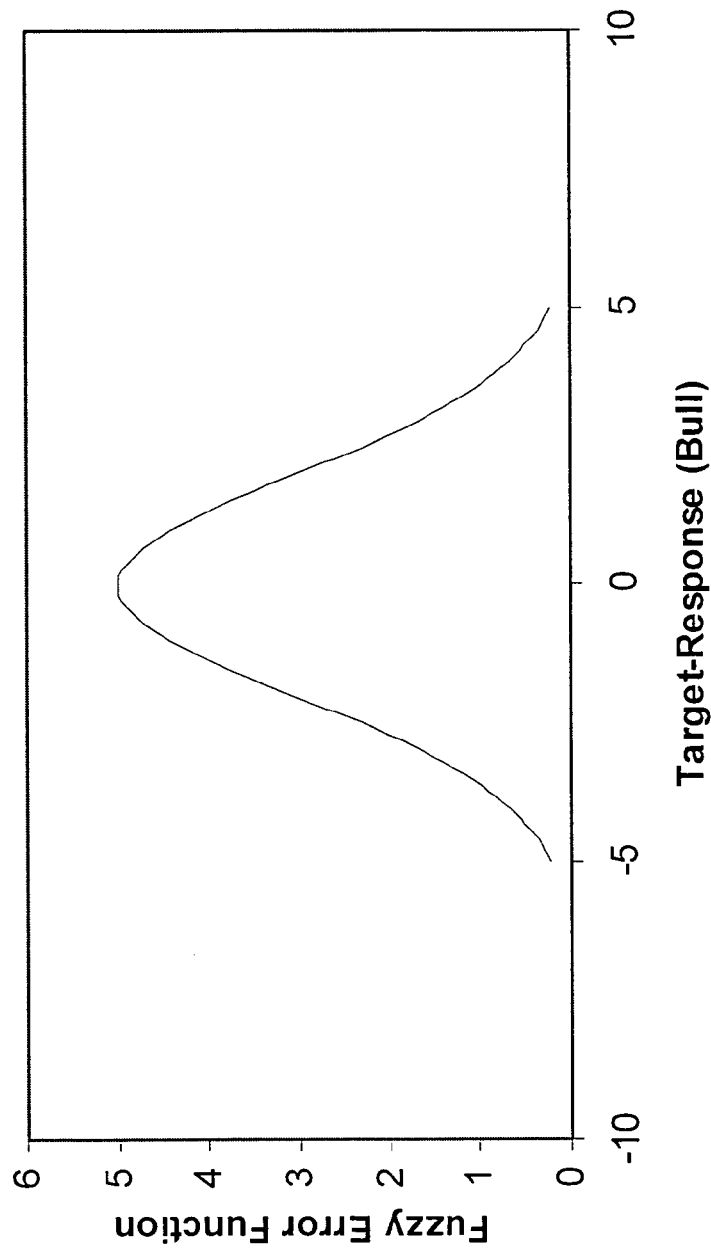
FIG. 2 is a graph of a fuzzy logic Gaussian correlation function against target-response (Bull) employed in the system and method of the present invention.

A Gaussian correlation function ($F_c$), Equation 5A and FIG. 2, is used to describe the "correctness" of a given set of parameters impact on response to target, based on expert system analysis. The parameters A and σ from Equation 5A, stated below, represent the variables that are tuned to manipulate the Gaussian function to the correct amplitude and width for each parameter. The variables are adjusted based on the confidence of the target and size of the allowable range from Table 1A or 1B.

$$F_c(X) = Ae^{\frac{-X^2}{2\sigma^2}} \quad \text{(Eq. 5A)}$$

Figure 2A:
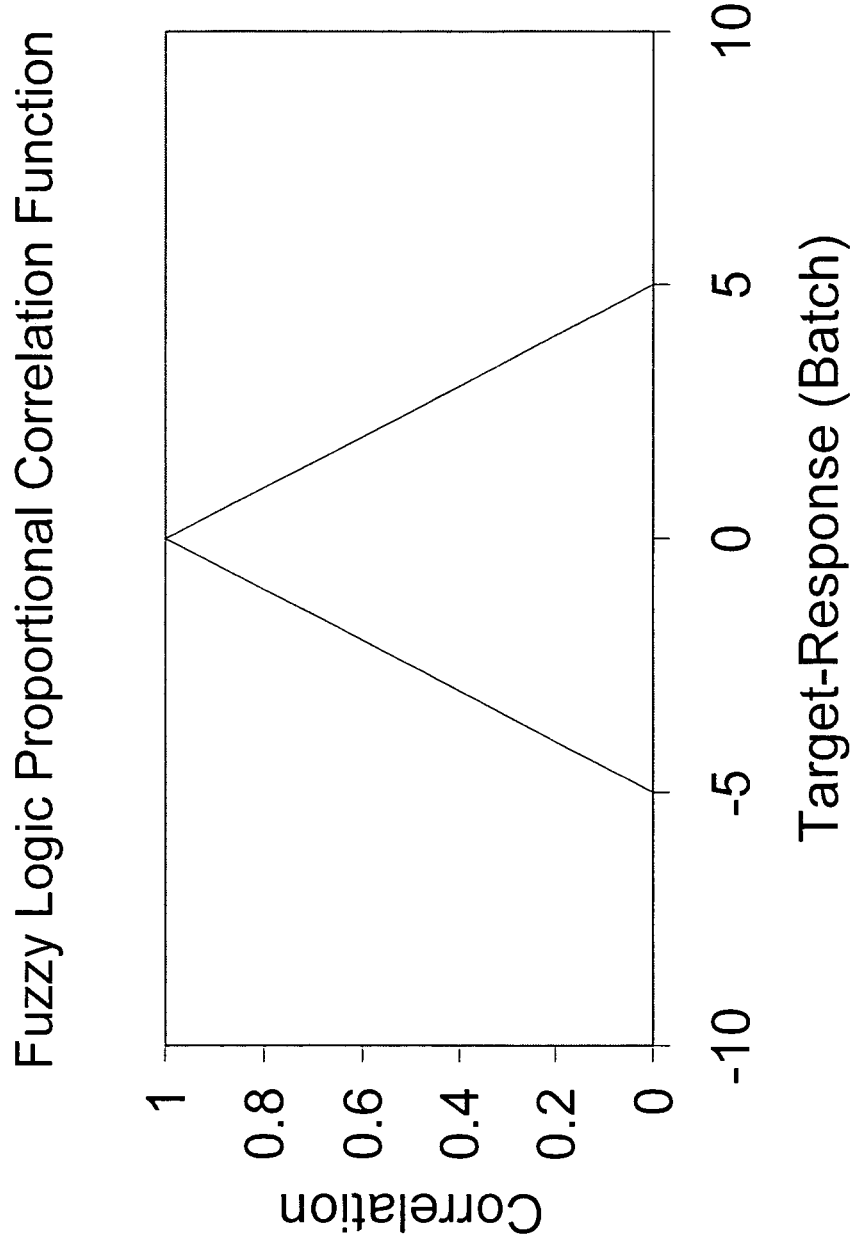
FIG. 2A is a graph of a fuzzy logic proportional correlation function against target-response (Bull) employed in the system and method of the present invention.

An alternative to a Gaussian function is a proportional function. The proportional function is similar to the Gaussian function, except that it has a linear response with slope m and y-intercept A, as shown in FIG. 2A where Fc(X)=0 if |X|>5. The relationship for the proportional function is shown in Equation 5B with effective limits so that Fc(X)=0 if |mX|>A.

$$F_c(X) = m|X| + A \quad \text{(Eq. 5B)}$$

Fuzzy logic correlation functions have a maximum peak at the optimal target response and decline as the response moves away from optimal. FIG. 2 shows the use of a Gaussian correlation function, where the input is with respect to reference target A=1, Sigma=2. FIG. 2A shows the use of a proportional correlation function, where the input is with respect to reference target A=1, Slope=0.2.

Training the fuzzy system provides a means to optimize the parameters so that small changes in a parameter with a wider range have less impact on the total variation measured. Manipulating values of A will impact the amplitude of the function and will provide higher (>1) or lower (<1) relative impact to the remaining parameters. Manipulating values of a will impact the width of the curve, with larger values providing a basis for larger variation from target before impacting the result, and smaller values having a quicker impact on the resulting value.

The gradient descent algorithm (see, Haykin, Simon, "Neural Networks: A Comprehensive Foundation" (2nd Edition), 1998) preferably used in the method of the present invention provides a technique to find minima of a function while only having knowledge of the function in a region close to current position. The general approach is to start at a location (no prior knowledge is needed for starting point, but the algorithm will converge more quickly as one starts closer to the minima) and determine the slope of the function at that location. The slope is used to determine the direction to travel towards the minima and the magnitude of the step. A scalar multiplier can be applied to the slope magnitude to accelerate or temper the size of the step. Small steps will require longer time to converge, while large steps are more likely to move too far and could cause oscillations around the minima.

Gradient descent relates to Equations 2-4, since there is no closed form solution to find the minima. The idea is that MCHC can be increased by increasing HGB, or by decreasing RBC and/or MCV. Evaluation of MCH will provide information unrelated to MCV, while evaluation of HCT will provide information unrelated to HGB. By moving in the right direction on RBC, MCV, and/or HGB, an optimal response can be obtained for all of these calculated relationships.

One common pitfall to the gradient descent algorithm can manifest if there are local minima in the function where the algorithm could get stuck and never reach the global minima. The benefit of the system of equations that are trying to be minimized by the method of the present invention is that local minima are not present, since the relationships are all first order, and the logic should always converge at the global minima.

Figure 3:
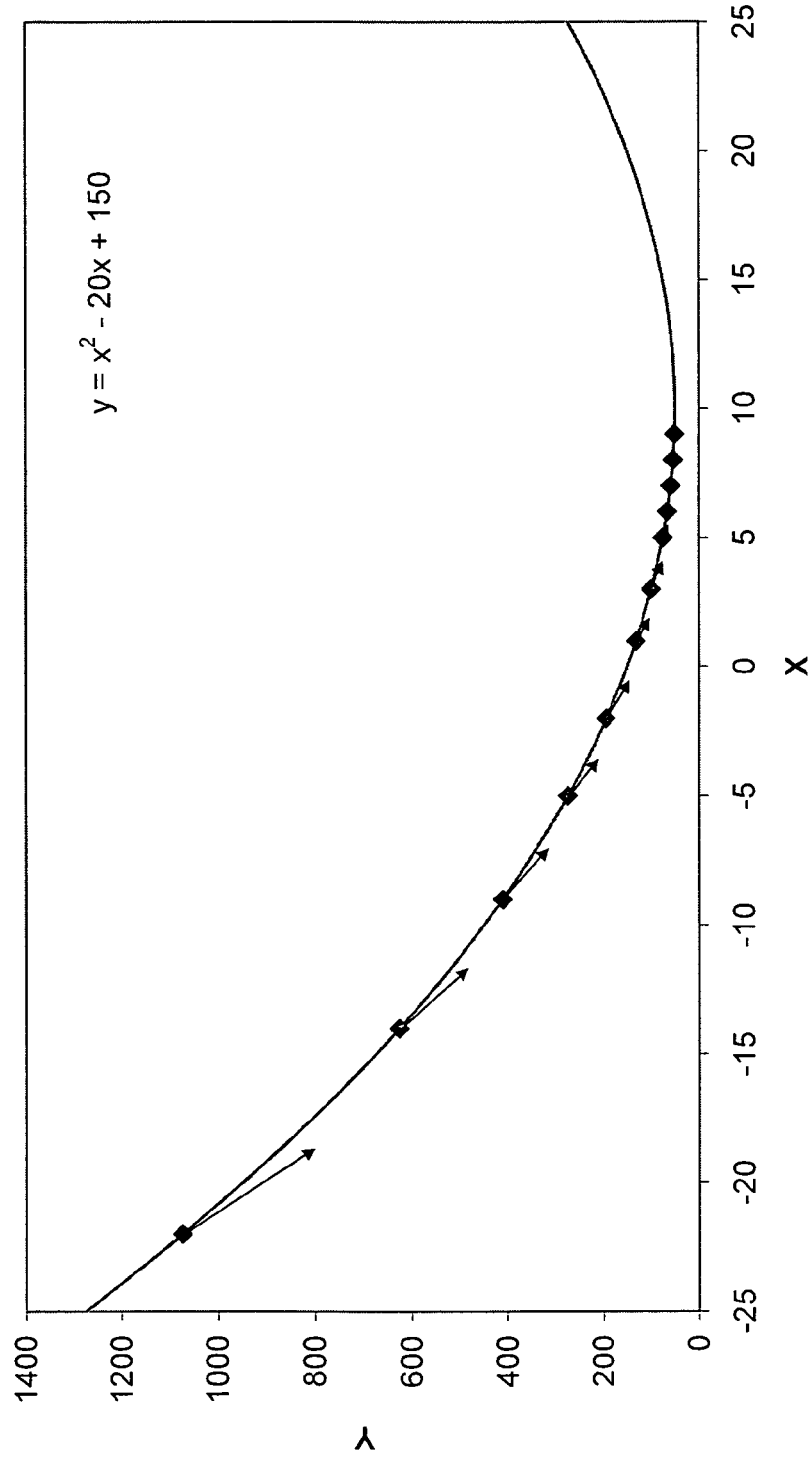
FIG. 3 is a graph of a gradient descent model having the relationship: $Y=(X-10)^2+50$, where Y is the ordinate and X is the abscissa, with a gradient factor equal to 0.1 for derivative, which is an example of a gradient descent model that is preferably used in the method and system of the present invention for function minima convergence.

An example of a quadratic function and associated values identified using the gradient descent algorithm preferably used in the present invention is shown in FIG. 3. It is clear by the size and direction of the movement arrows that the algorithm makes large steps when far from the minima, and makes less aggressive movements as it gets closer to the minima. This approach employed by the present invention will provide a way to optimize RBC, MCV, and HGB with criteria related to the HCT, MCH, and MCHC responses. Fuzzy logic is preferably used in the method of the present invention to provide weighting with respect to the differences between responses and species specific targets. The Gaussian functions defined in Equation 5 are used in the method as inputs to the correlation function ($F_C$), shown in Equation 6. The correlation function takes the result of the N Gaussian functions for each parameter (RBC, MCV, HGB, HCT, MCH, MCHC) as a function of Bull batch. The outcome is a single value that defines how correlated the results are based on the adjustments. Optimizing this correlation function output value in accordance with the present invention will provide the basis for the gradient descent minimizing algorithm.

$$F_C = \sqrt{\frac{\sum_{n=1}^{N} FuzzyFunction(n)^2}{N}} \quad \text{(Eq. 6)}$$

Figure 3A:
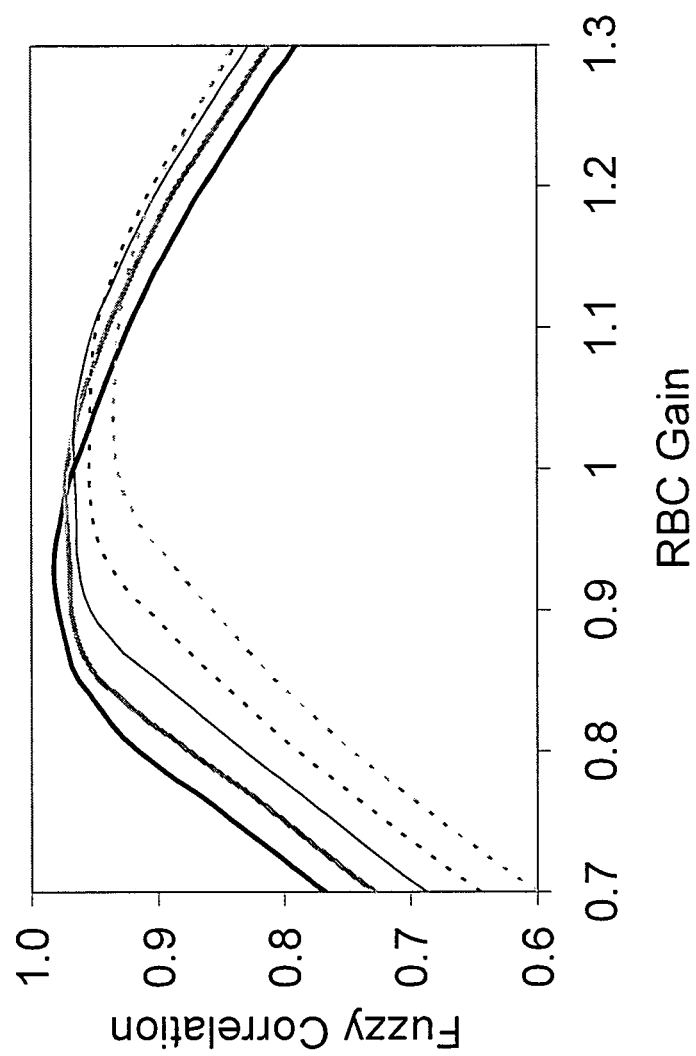
FIG. 3A is a graph of correlation functions plotted against RBC gain for different values of HGB.
Figure 4A:
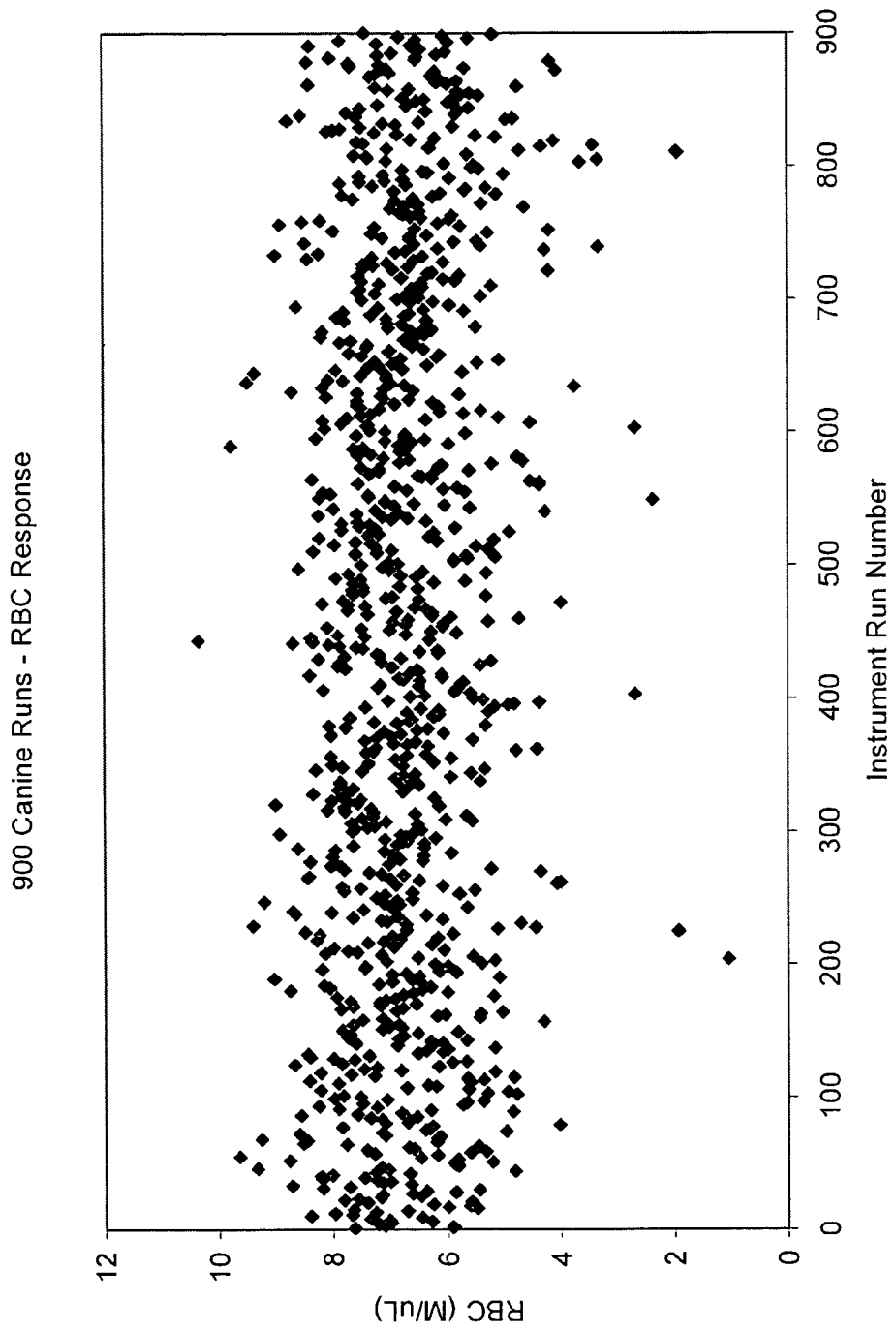
FIG. 4 is a set of graphs plotting the raw patient sample results for a diagnostic analyzer running canine samples. The gray dots represent patient results in time series order. Targets for Bull adjustments and reference ranges for Westgard Rules are shown in black, where appropriate. More specifically, FIG. 4(a) plots RBC (red blood cells) against instrument runs.
FIG. 4(b) plots MCV (mean corpuscular volume) against instrument runs.
FIG. 4(c) plots HGB (hemoglobin) against instrument runs.
FIG. 4(d) plots HCT (hematocrit) against instrument runs.
FIG. 4(e) plots MCH (mean corpuscular hemoglobin) against instrument runs.
FIG. 4(f) plots MCHC (mean corpuscular hemoglobin concentration) against instrument runs.
Figure 4B:
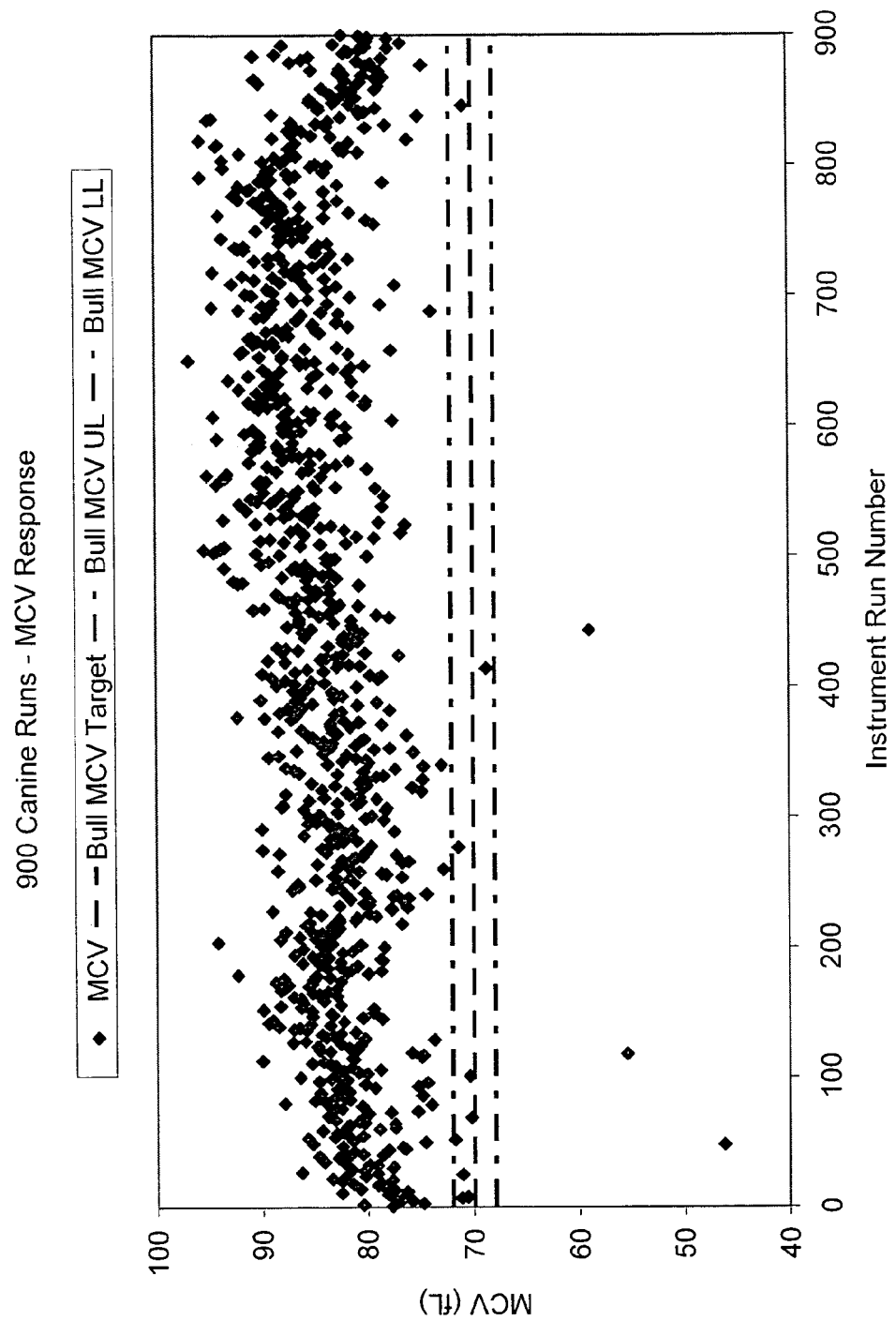
Figure 4C:
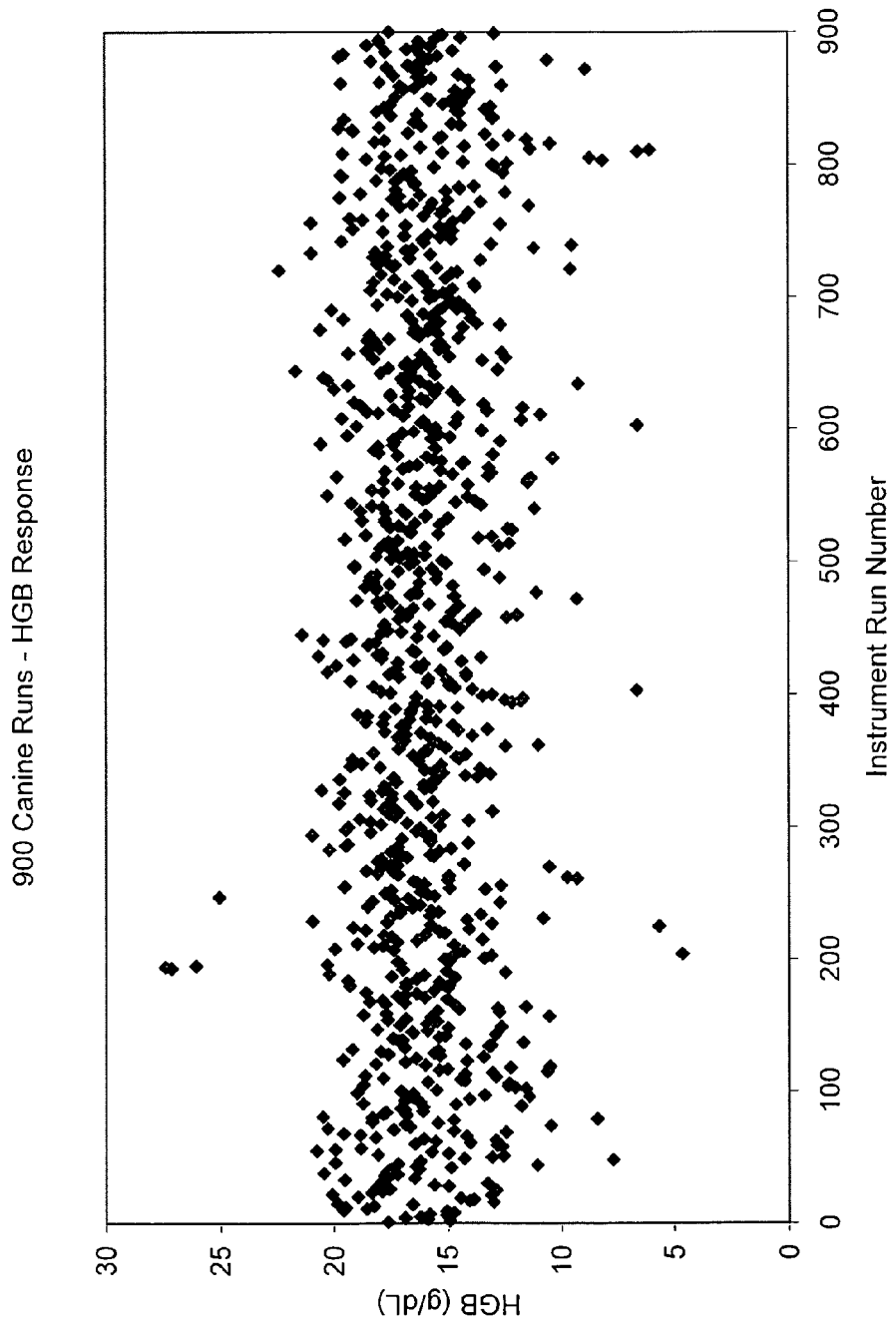
Figure 4D:
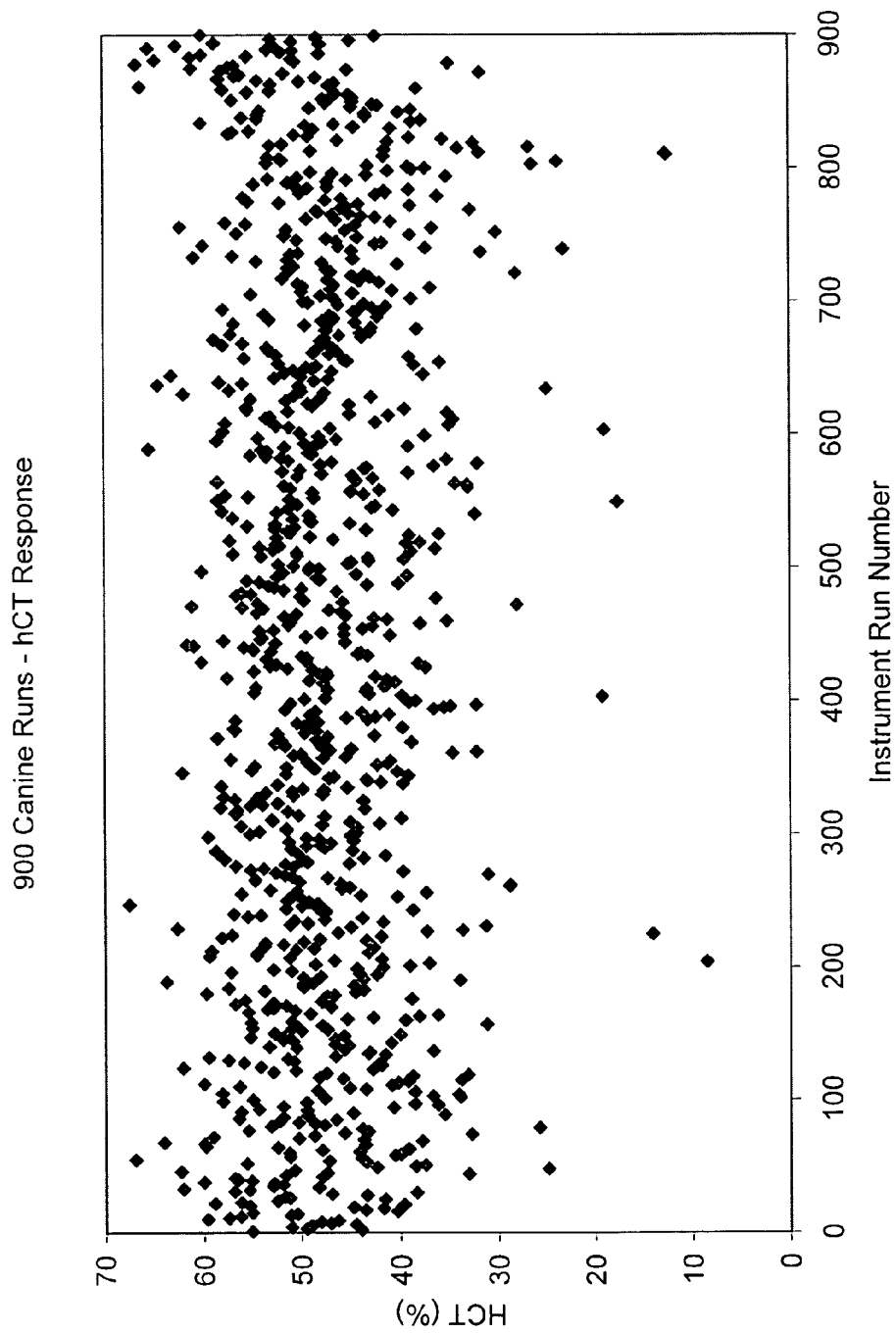
Figure 4E:
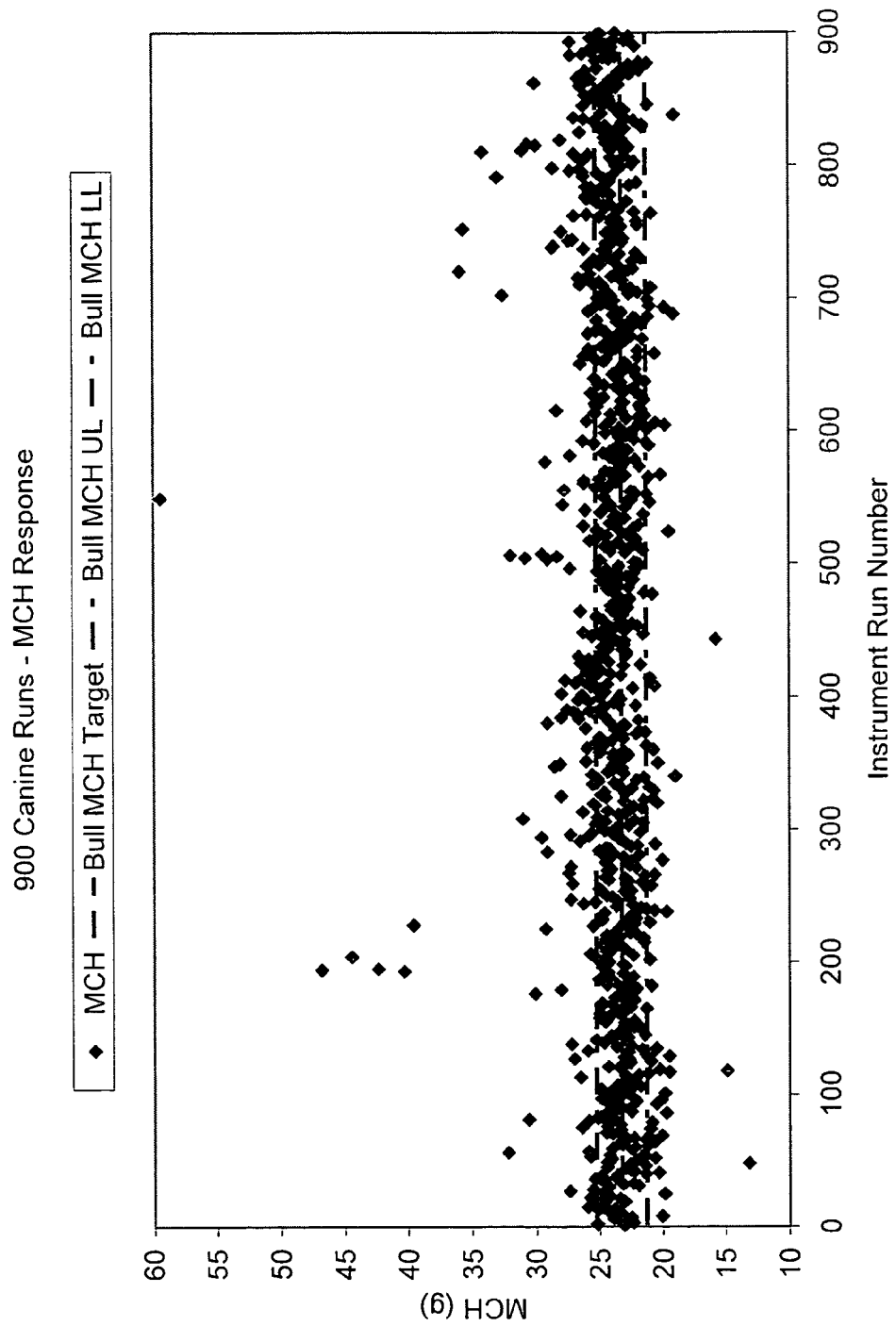
Figure 4F:
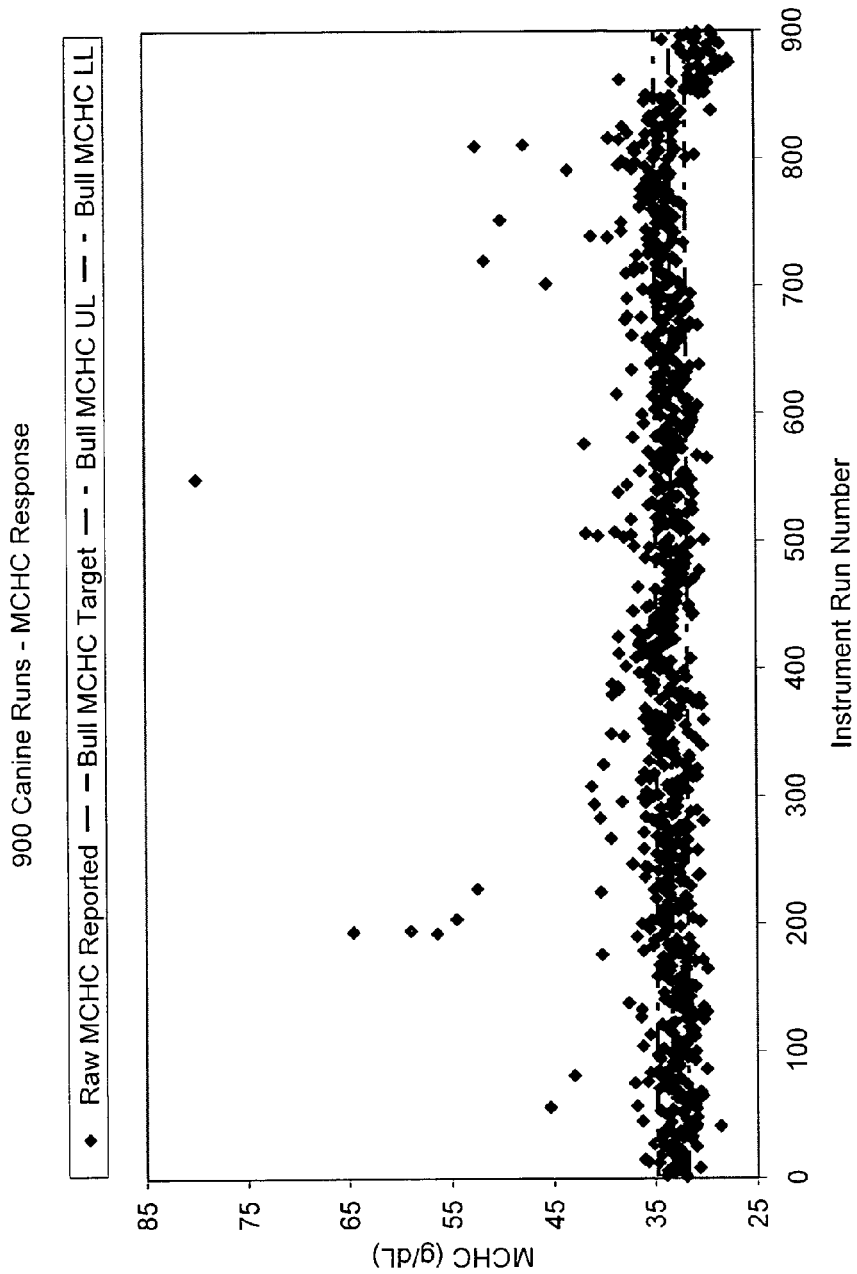
Figure 5A:
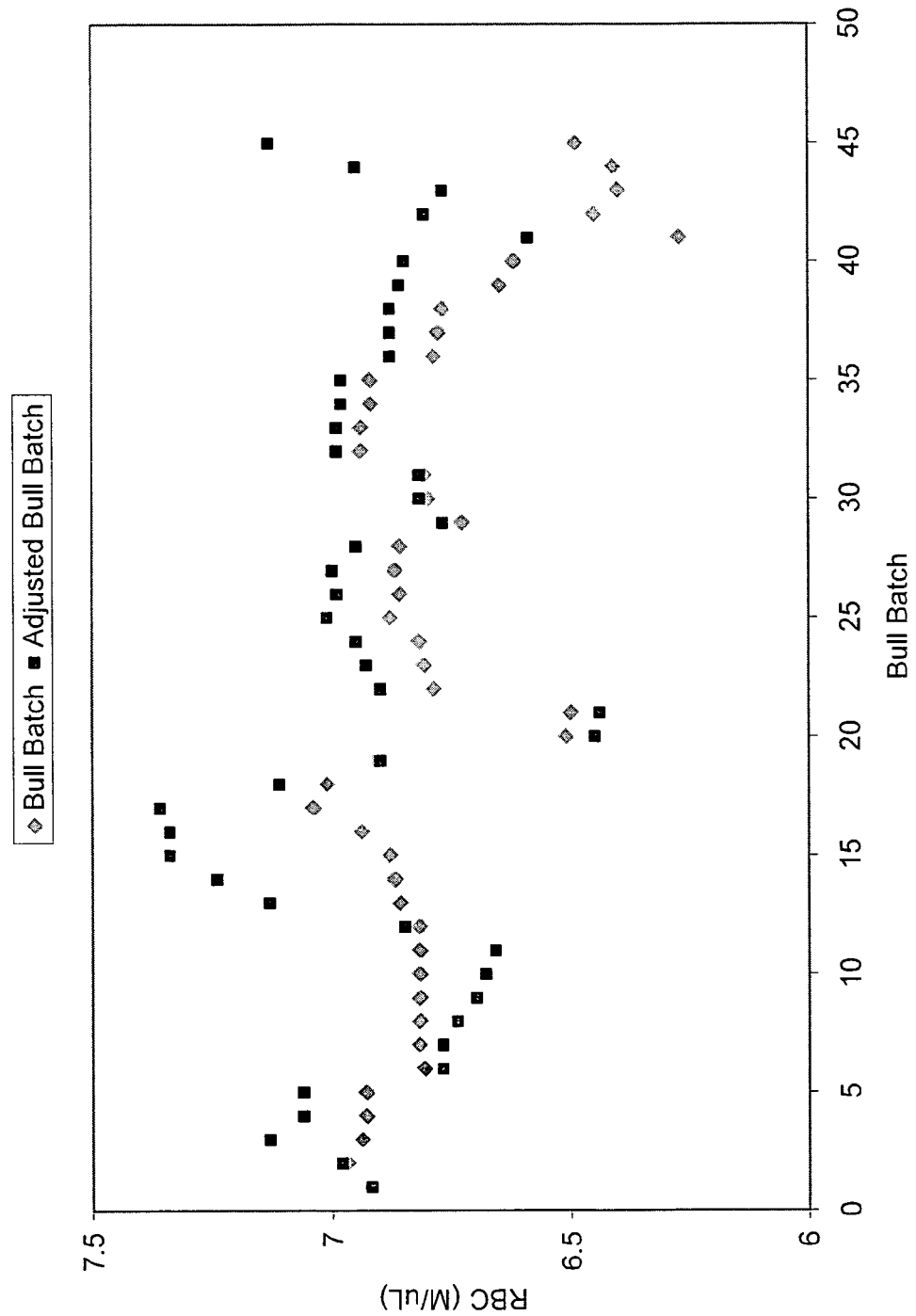
FIG. 5(a) plots RBC against Bull batch numbers.
Figure 5B:
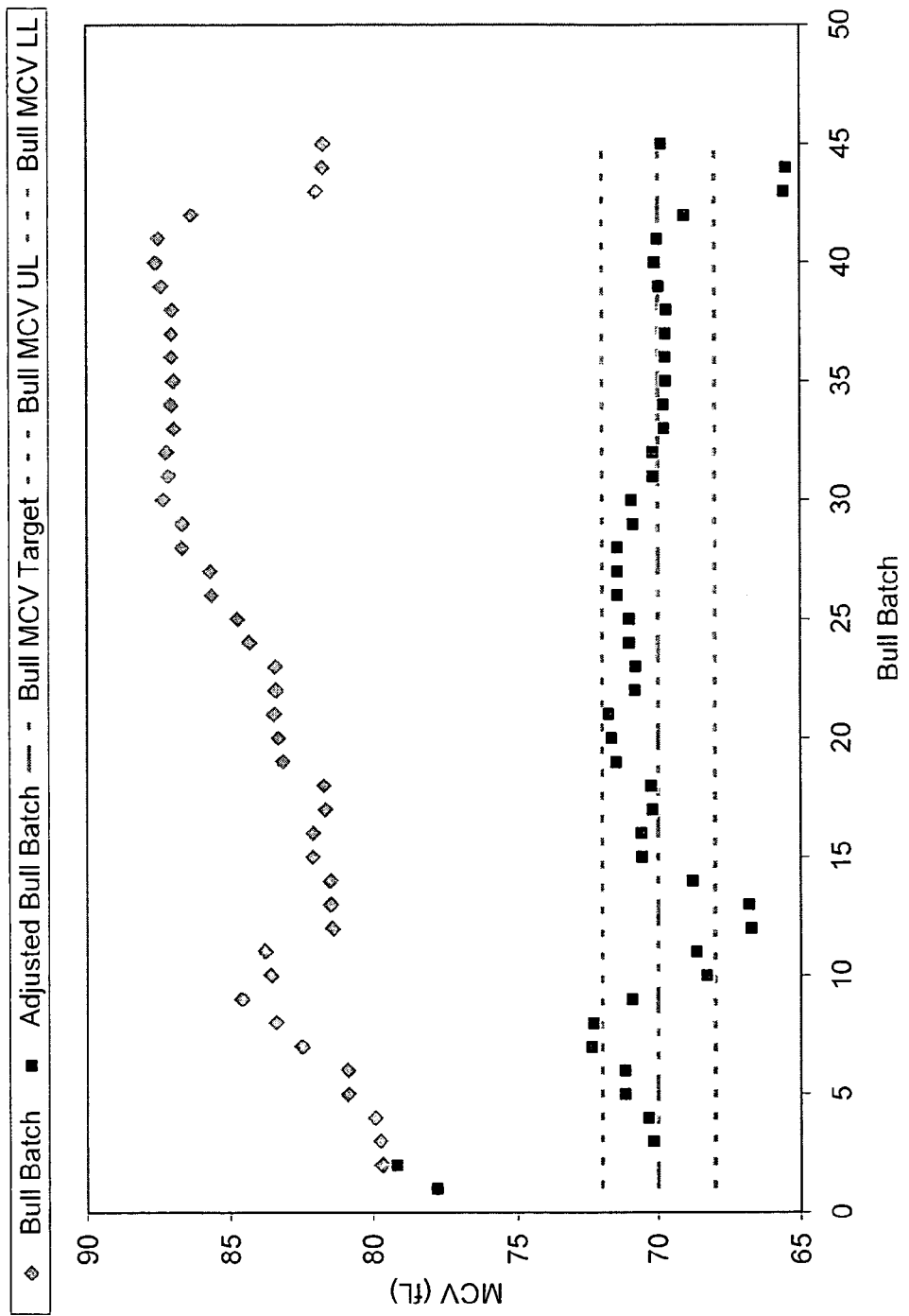
FIG. 5(b) plots MCV against Bull batch numbers.
Figure 5C:
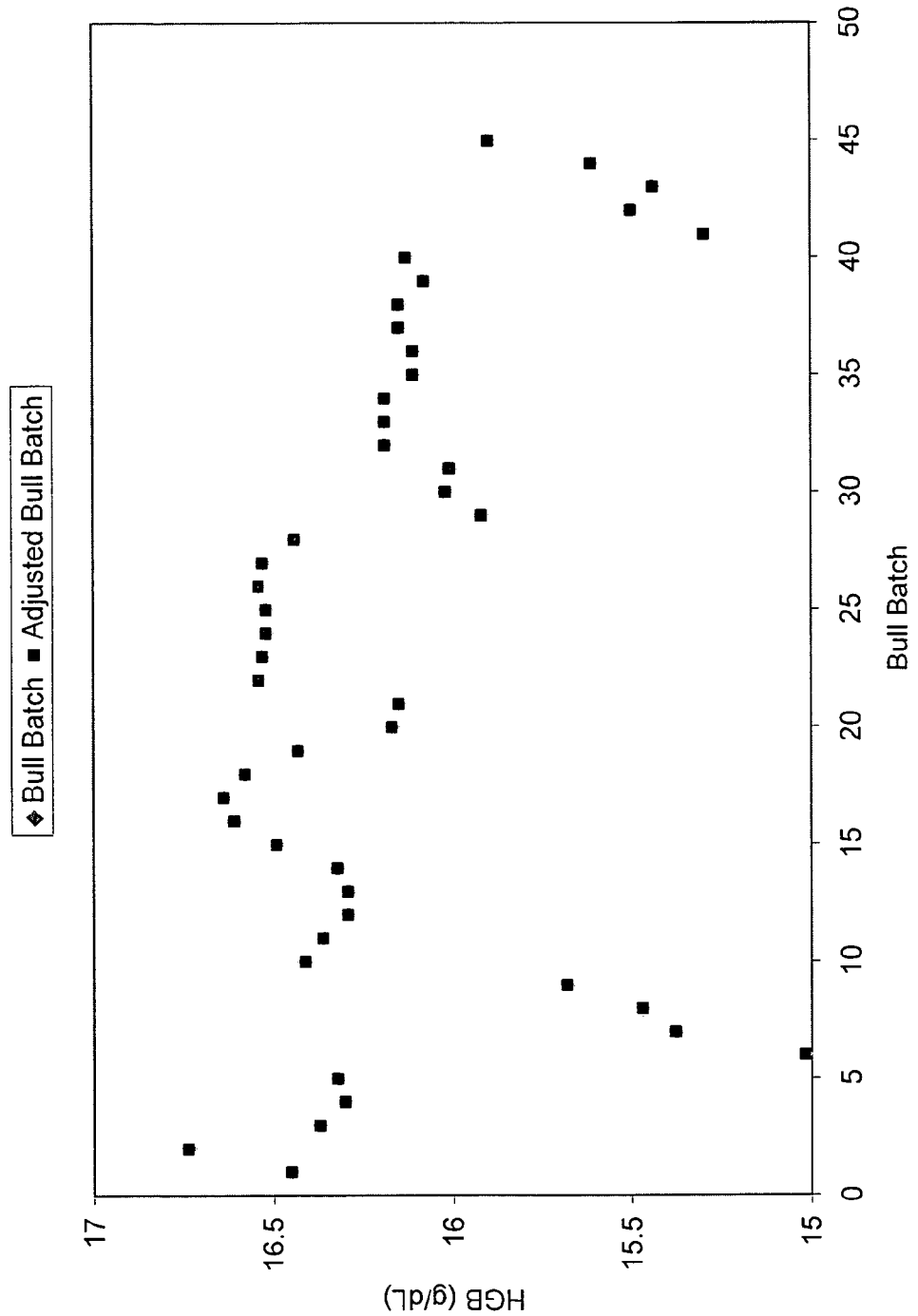
FIG. 5(c) plots HGB against Bull batch numbers.
Figure 5D:
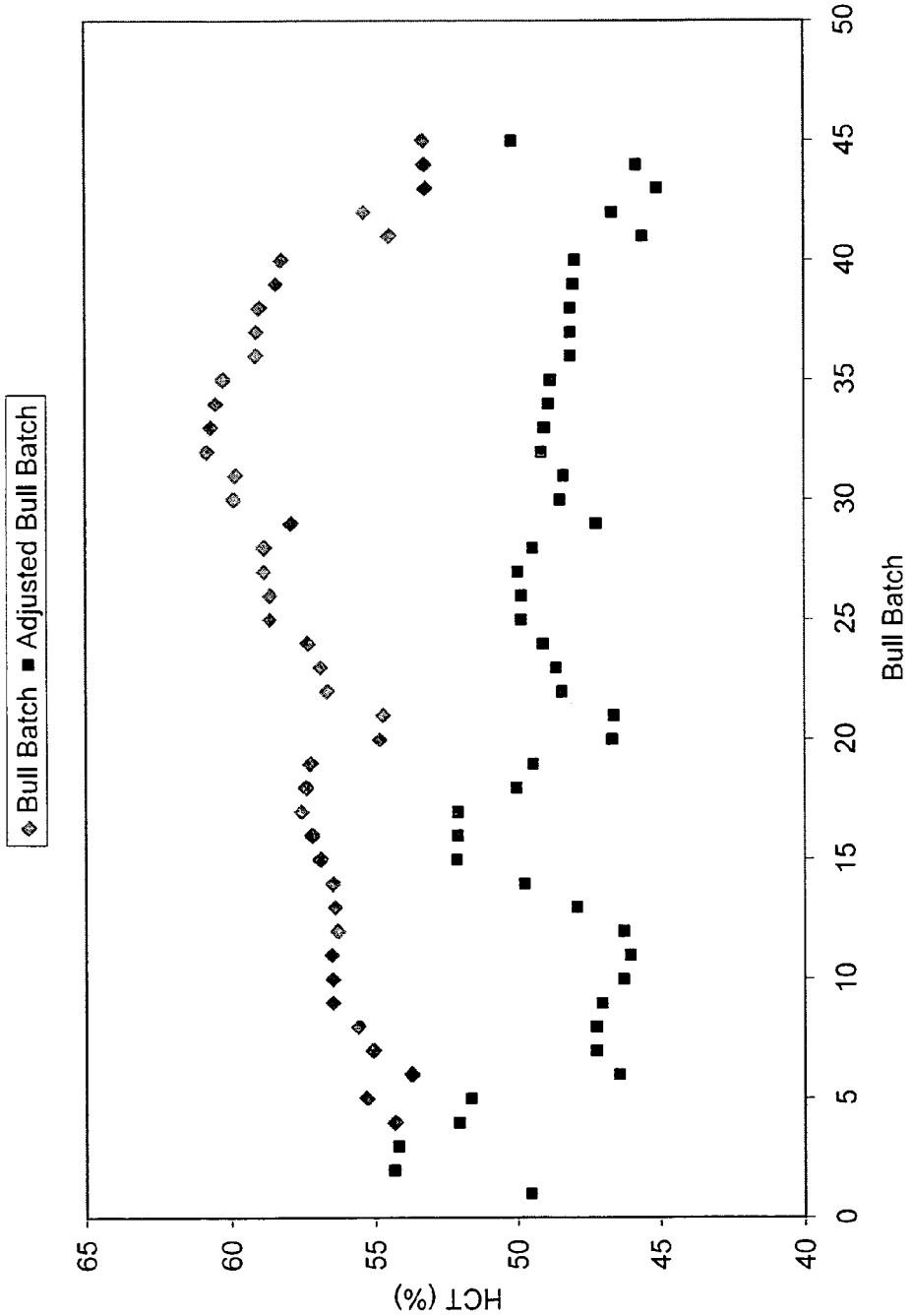
FIG. 5(d) plots against HCT against Bull batch numbers.
Figure 5E:
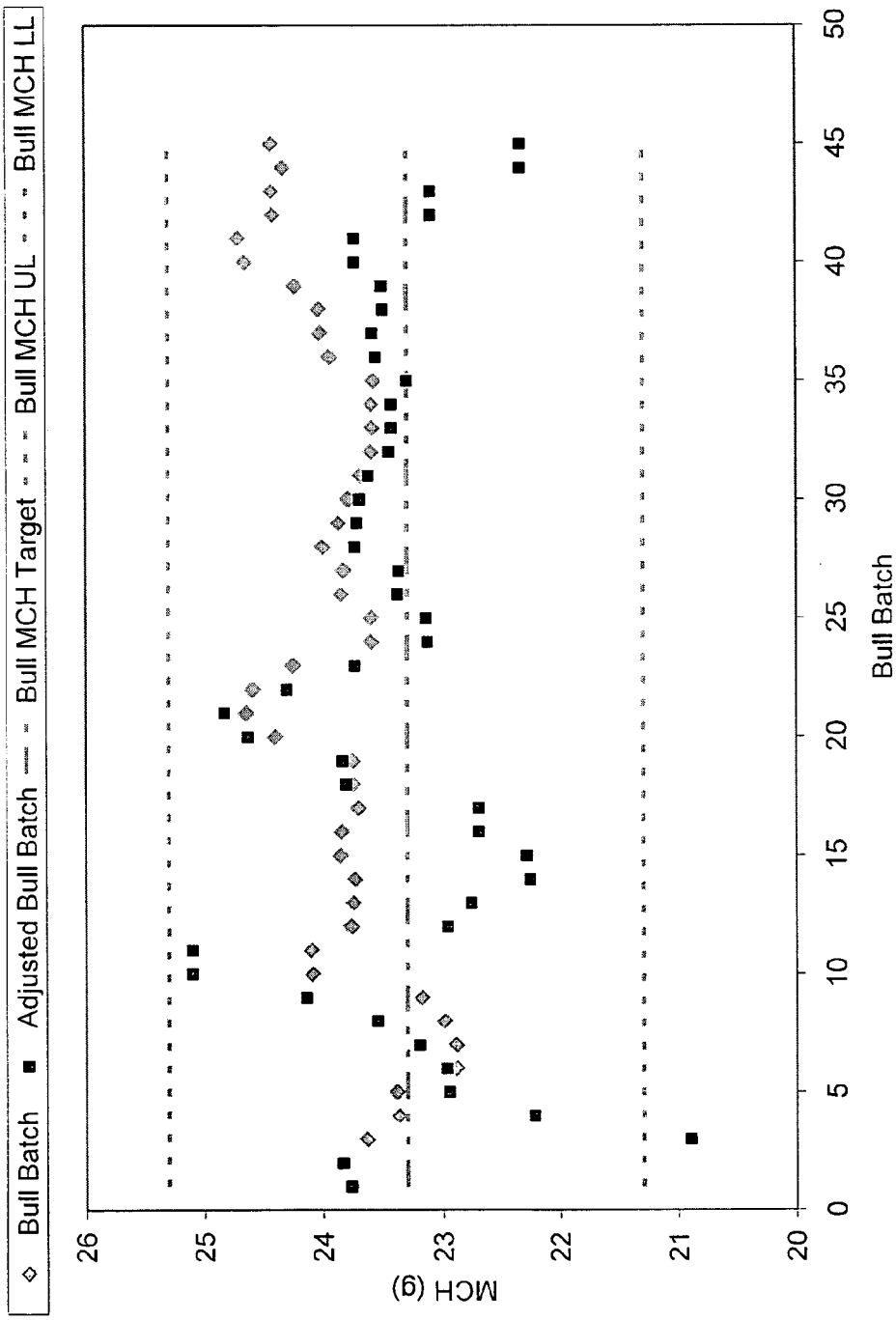
FIG. 5(e) plots MCH against Bull batch numbers.
Figure 5F:
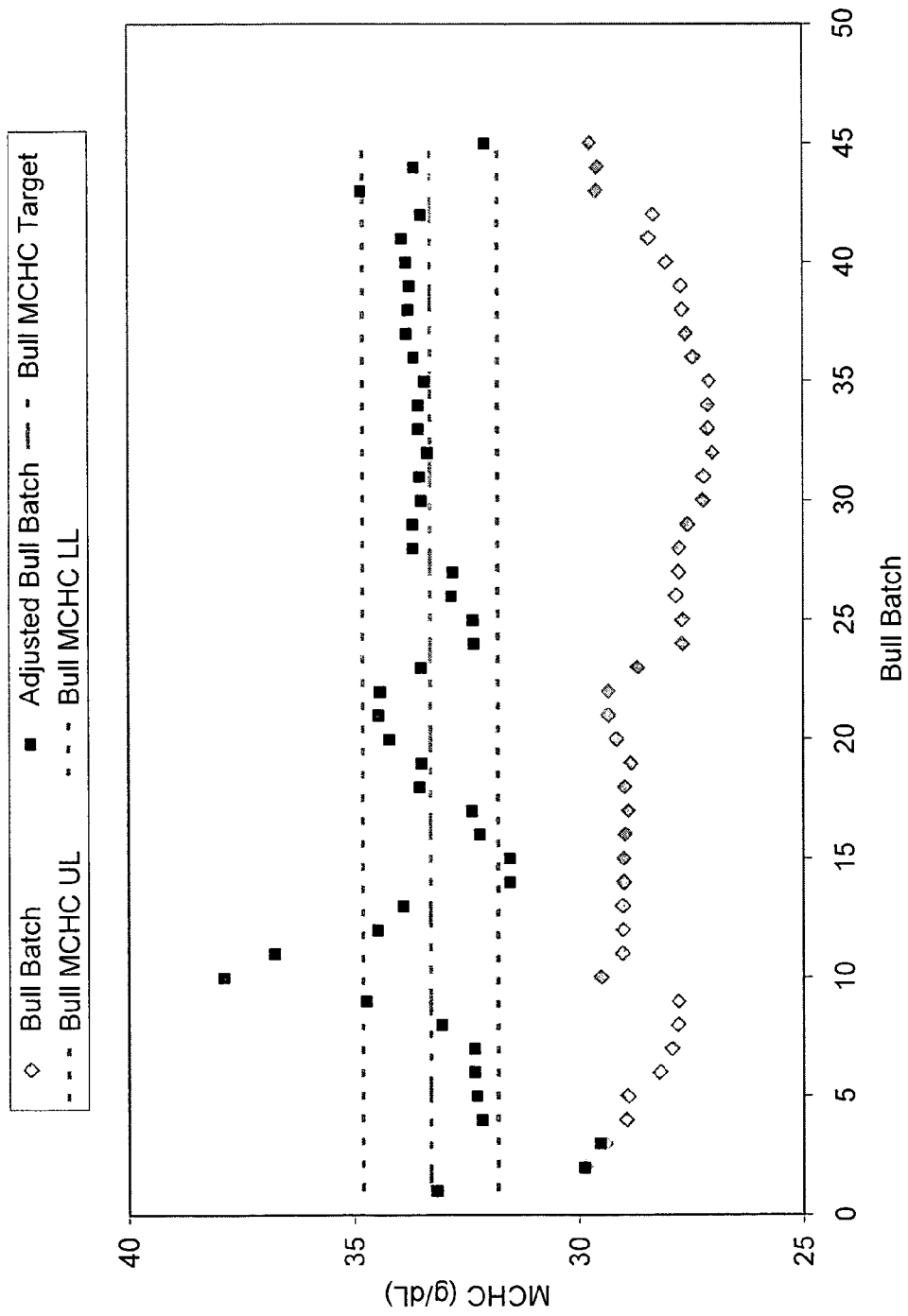
FIG. 5(f) plots MCHC against Bull batch numbers.

A 2-d gradient descent algorithm can be used to optimize RBC and HGB with respect to HCT, MCH, and MCHC, since MCV already has a target value. A representation of constant HGB curves for the 2-d map is shown in FIG. 3A. Translating these curves into the model used by gradient descent provides an example of the 2-d map as it is followed by the gradient descent algorithm, shown in FIG. 3B. At every point, the value at all eight nearest neighbor positions is evaluated and moved to the largest value until the center point is the largest value.

Thus, FIG. 3A is a graph of the correlation functions. Each curve represents constant HGB and the Fuzzy Logic correlation function while varying RBC by a factor ranging from 0.7 to 1.30. HGB factor range is 0.90 to 1.10. The thick solid black line represents HGB at 0.90, thick solid gray line represents 0.95, solid black line represents 1.00, black dotted line represents 1.05, and the gray dotted line represents 1.10.

FIG. 3B is a chart of a 2-d gradient descent fuzzy correlation function based on effective results of adjustments on RBC, MCV, and HGB with correlated calculated parameters HCT, MCH, and MCHC. Gradient descent map starting from (1,1), no adjustment to RBC and HGB, and moving to optimal location.

In the example described previously to illustrate the method of the present invention, the same dataset used in FIG. 4 is then analyzed with Westgard Rules, defined above, a gradient descent algorithm and fuzzy logic to define adjustments in the analyzer's patient hematology results and then calculate updated instrument results and Bull batches. FIG. 5 shows the results before and after adjustment to these results, in accordance with the present invention. HGB was not adjusted based on the algorithm, and the data points completely overlap for raw Bull batches and adjusted Bull batches.

The system logic of the present invention made a slight change to RBC, a more significant change to MCV, and no change to HGB. HCT was stabilized and matched PCV (packed cell volume).

Figure 6:
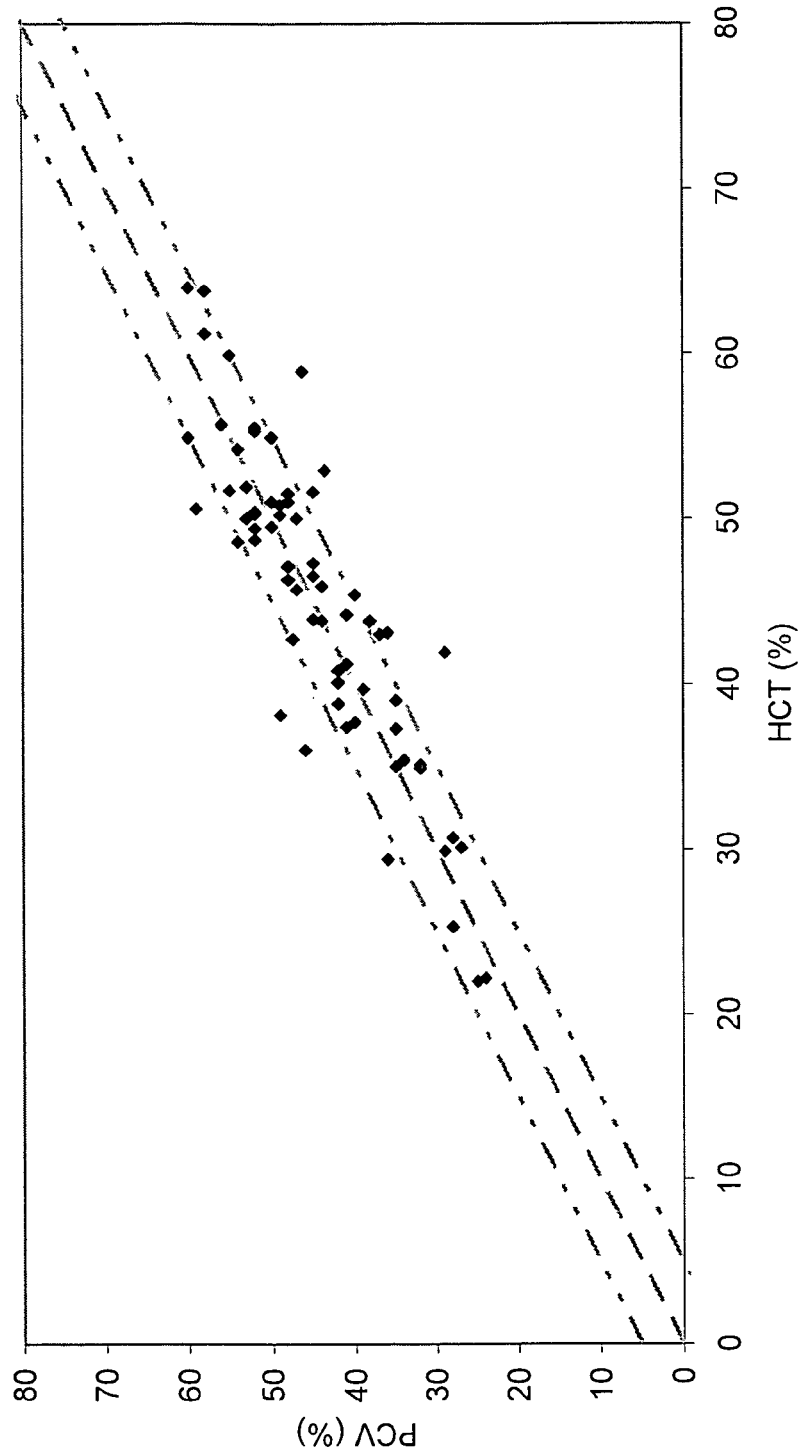

FIG. 6 shows a series of instruments reported HCT vs. PCV after Bull adjustments were implemented in accordance with the present invention. MCH and MCHC show marked improvement and match within targets well, as shown in FIG. 5.

Figure 7:
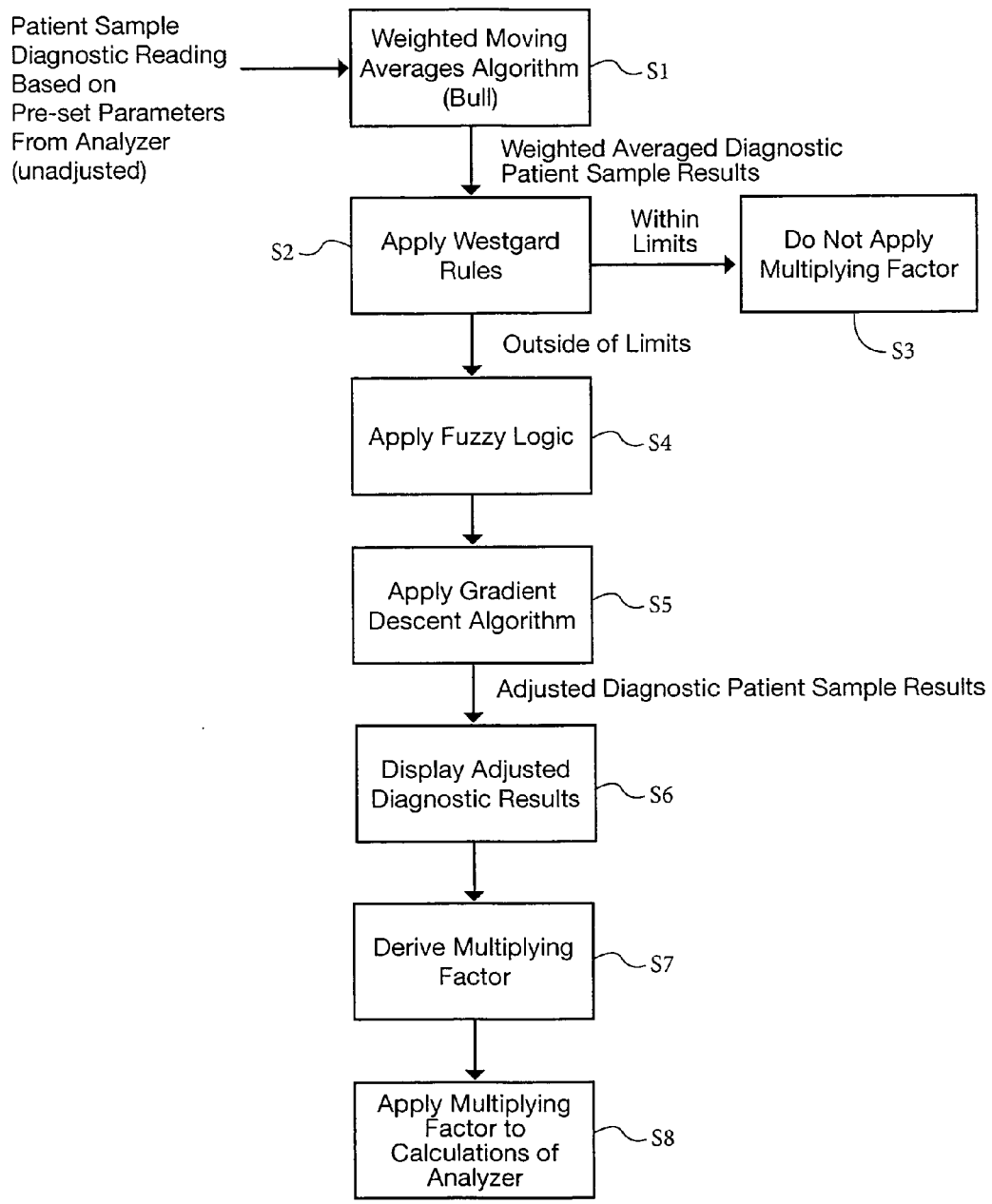
FIG. 7 is a flow chart showing the operation of the system and method of the present invention for real time, automated calibration of a diagnostic analyzer.

FIG. 7 is a simplified flow chart illustrating the operation of the automated system of the present invention for calibrating a diagnostic analyzer, such as a hematology analyzer. The patient sample diagnostic readings resulting from the analyzer's calculations based on patient samples are acted upon in a subroutine in which a weighted moving averages algorithm is applied (Step S1). Preferably, this weighted moving averages algorithm is Bull's algorithm. The analyzer calculates the diagnostic results using the analyzer's pre-set parameters (such as optical gain, for example). This subroutine provides weighted averaged diagnostic results.

Then, Westgard Rules or any other SPC control chart rules are applied to the weighted averaged diagnostic results (Step S2). The control chart rules (or more preferably, Westgard Rules) create limits or ranges which are used to test the extent to which the weighted averaged diagnostic results reside within such limits or ranges. Thus, the weighted averaged diagnostic results are compared in Step S2 with such control chart rule limits or ranges. If the weighted averaged diagnostic results fall within the control chart rule limits or ranges, then no multiplying factor is applied to the patient sample diagnostic results calculated by the analyzer using its pre-set parameters (e.g., optical gain) (Step S3).

However, should the weighted averaged diagnostic results fall outside of the control chart rules limits or ranges during such a comparison in Step S2, then the method and system of the present invention apply fuzzy logic (Step S4) and a gradient descent algorithm (Step S5) to the weighted averaged diagnostic results to obtain adjusted diagnostic results of the patient samples which are now within the acceptable limits or ranges of the control chart rules. Such adjusted diagnostic results are read out or displayed by the analyzer (Step S6) and represent a more accurate calculation of the patient sample diagnostic results.

Also, one or more multiplying factors are derived from the application of the fuzzy logic (Step S4) and the gradient descent algorithm (Step S5) to the weighted averaged diagnostic results (Step S7). As shown in Step S8, the multiplying factor (or factors) is used in modifying the calculations performed by the analyzer with its pre-set parameters to correct the results of such calculations without the need to actually change the analyzer's pre-set parameters stored in the analyzer's memory. Thus, for example, by applying the derived multiplying factor, the overall gain to the analyzer's optical system may be effectively adjusted from 1.03 to 1.04 to more accurately provide patient sample diagnostic results read out or displayed by the analyzer.

The calibration method is preferably applied each time the diagnostic analyzer generates patient sample results so that the calculated results may be automatically adjusted in real time, and the multiplying factor (which is applied to the analyzer's pre-set parameters) may be continually changed as is required, in order to provide more accurate patient readings.

Figure 7A:
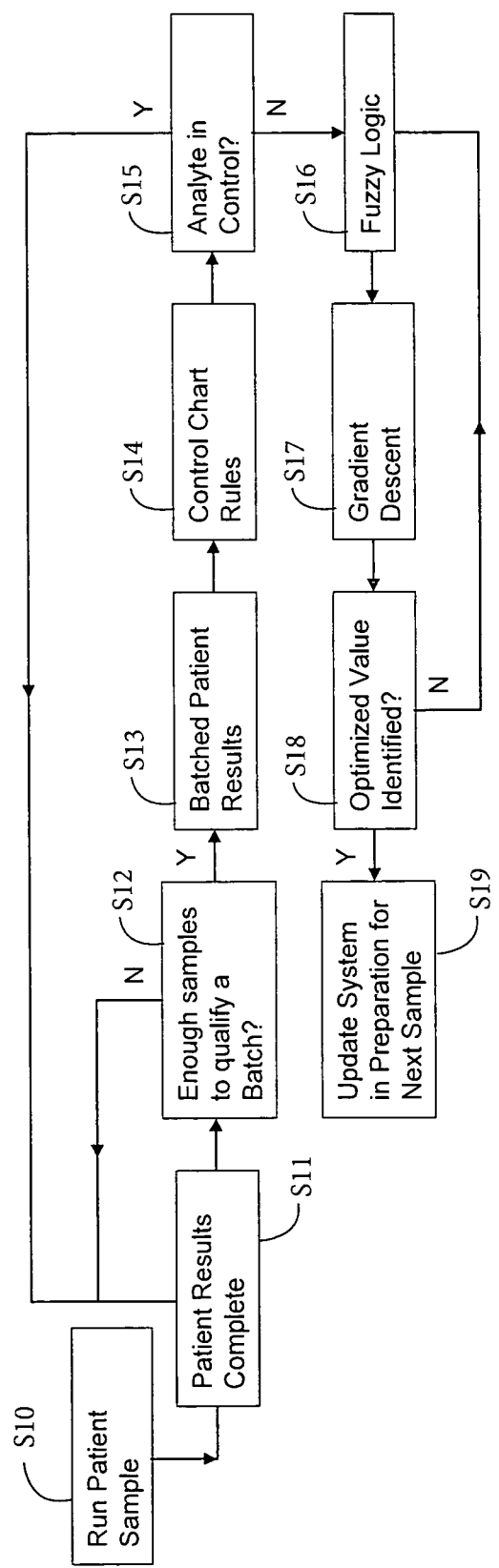
FIG. 7A is another flow chart showing an alternative operation of the system and method of the present invention for real time, automated calibration of a diagnostic analyzer, and further illustrating the preferred iterative process in applying fuzzy logic and a gradient descent algorithm until an optimized value is achieved.

FIG. 7A is another simplified flow chart illustrating an alternative operation of the automated system of the present invention for calibrating a diagnostic analyzer. The first step in the process is to run the patient sample (Step S10). After the patient results are complete (Step S11), the automated system of the present invention makes a determination as to whether there are enough samples to qualify a batch, such as a Bull's batch (Step S12). If there are not enough samples to qualify a batch, then the system obtains additional patient results (Step S11). However, if there are enough samples to qualify a batch, then the patient results are batched (Step S13), in accordance with the method of the present invention. Now, control chart rules, such as Westgard Rules, are applied to the batched patient results (Step S14).

Then, in accordance with the method of the present invention, the automated system determines whether the patient diagnostic results reside within the limits or ranges created by the control chart rules (Step S15). If the patient diagnostic results are within such control limits or ranges, then no further correction is required to the diagnostic results and, accordingly, the patient results are complete and may be output by the automated system (Step S11). However, if the patient diagnostic results fall outside of the control chart rules limits or ranges in Step S15, then fuzzy logic (Step S16) and a gradient descent algorithm (Step S17) are applied to the diagnostic results to obtain adjusted patient diagnostic results.

If the automated system of the present invention determines that the adjusted diagnostic results are not optimized (Step S18), then fuzzy logic (Step S16) and the gradient descent algorithm (Step S17) are repeatedly applied to the adjusted diagnostic results. If the automated system determines that an optimized value has been achieved (Step S18), then a multiplying factor is used in modifying the calculations performed by the analyzer with its pre-set parameters without the need to actually change the analyzer's pre-set parameters stored in the analyzer's memory, and this multiplying factor will be applied by the automated system of the present invention for the next patient sample (Step S19).

Figure 8:
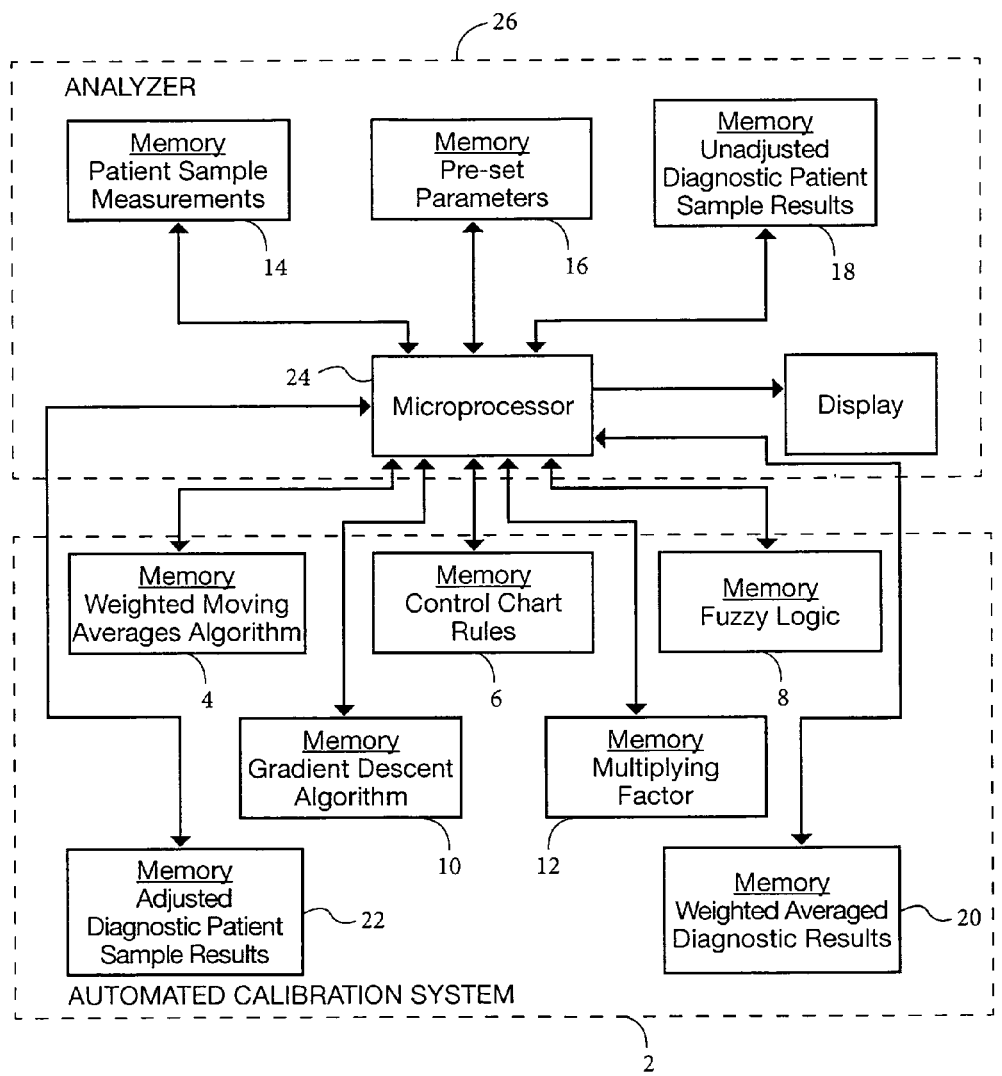
FIG. 8 is a block diagram of an automated system for calibrating a diagnostic analyzer formed in accordance with the present invention, and illustrating the cooperation between the system and the diagnostic analyzer.

FIG. 8 is a block diagram of one form of a system 2 which implements the automated calibration method of the present invention. This system 2 can be realized by software, or more precisely, an application program, or by firmware or hardware. The system 2 may include a memory 4, such an EEPROM (electronically erasable programmable read only memory) in which is stored the weighted moving averages algorithm, a memory 6 in which is stored the control chart rules, a memory 8 in which is stored the fuzzy logic, a memory 10 in which is stored the gradient descent algorithm and a memory 12 in which is stored the multiplying factor. Memories or storage devices are also provided for storing patient sample measurements determined by the analyzer (memory 14), the pre-set parameters of the analyzer (memory 16), the unadjusted diagnostic results of patient samples calculated by the analyzer using the pre-set parameters (e.g., optical gain) of the analyzer (memory 18), the weighted averaged diagnostic results (memory 20) resulting from the application of the weighted moving averages algorithm, and the adjusted or corrected diagnostic patient sample results (memory 22) resulting from the application of the fuzzy logic and the gradient descent algorithm. A microprocessor, microcontroller or CPU 24 may be employed to carry out the application of the weighted moving averages algorithm, the control chart rules, the fuzzy logic and the gradient descent algorithm to the patient data, or make any comparisons to determine if the weighted averaged diagnostic results are within the control chart rule limits or ranges, and derive the multiplying factor to be applied to the analyzer's pre-set parameters. Of course, it should be realized that such structure (e.g., memories, microprocessor and the like) may already exist within the analyzer 26, and such structure may be conveniently utilized in performing the functions of the automated calibration method of the present invention.

Figure 9:
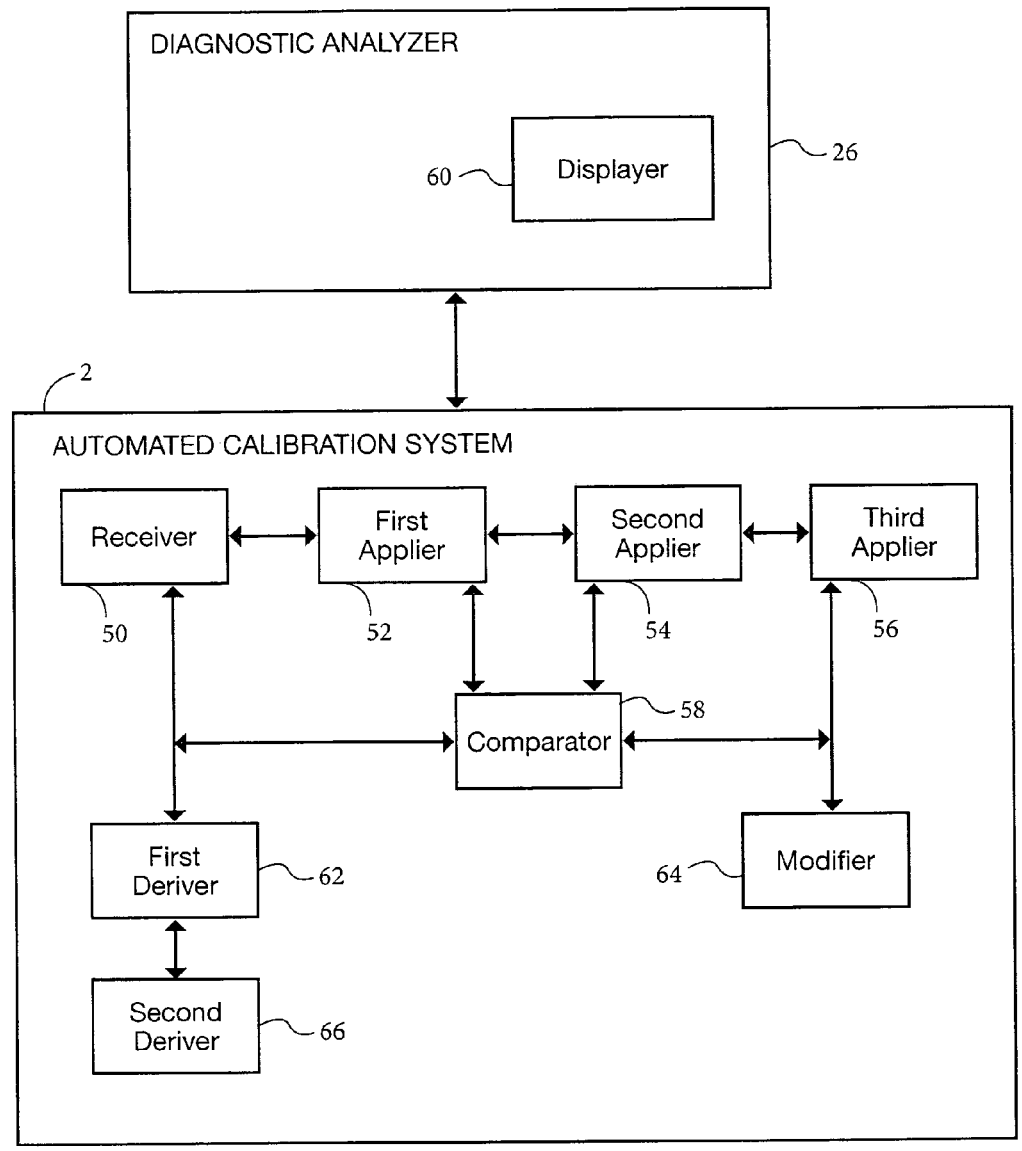
FIG. 9 is a block diagram of an alternative embodiment of an automated system for calibrating a diagnostic analyzer formed in accordance with the present invention, and illustrating the cooperation between the system and the diagnostic analyzer.

FIG. 9 is a block diagram of a second form of a system 2 which implements the automated calibration method of the present invention. The automated system calibrates in real-time a diagnostic analyzer 26, where the diagnostic analyzer performing calculations on patient diagnostic samples using pre-set parameters. Preferably, the automated calibration system includes a receiver 50 which receives diagnostic results of patient samples calculated by the analyzer using the pre-set parameters of the analyzer, a first applier 52 which applies a weighted moving averages algorithm to the patient sample diagnostic results to obtain weighted averaged diagnostic results, and a second applier 54 which applies control chart rules to the weighted averaged diagnostic results, and which creates from the control chart rules limits or ranges which are used to test the extent to which the weighted averaged diagnostic results reside within such limits or ranges. The automated calibration system further includes a third applier 56 which selectively applies fuzzy logic and a gradient descent algorithm to the weighted averaged diagnostic results.

The automated calibration system of the present invention also includes a comparator 58 which compares the weighted averaged diagnostic results with such control chart rule limits or ranges. If the weighted averaged diagnostic results fall within the control chart rule limits or ranges, then a multiplying factor is not applied to the patient sample diagnostic results calculated by the analyzer 26 using its pre-set parameters. However, if the weighted averaged diagnostic results fall outside of the control chart rule limits or ranges during such a comparison, then the third applier 56 applies the fuzzy logic and the gradient descent algorithm to the weighted averaged diagnostic results to obtain adjusted diagnostic results of the patient samples which are now within the acceptable limits or ranges of the control chart rules.

The system further includes a reader or displayer 60 which reads out or displays such the adjusted diagnostic results by the analyzer 26. This reader or displayer 60 may form part of the analyzer. The automated calibration system also has a first deriver 62 which derives one or more multiplying factors from the application of the fuzzy logic and the gradient descent algorithm to the weighted averaged diagnostic results, and a modifier 64 which modifies the calculations performed by the analyzer 26 with its pre-set parameters by the multiplying factor (or factors) to correct the results of the analyzer 26 calculations without the need to change the analyzer's pre-set parameters.

In a further preferred form of the present invention, and as shown in FIG. 9, the third applier 56 of the automated calibration system applies Westgard Rules to the patient sample diagnostic results to obtain the weighted averaged diagnostic results. The automated system may further include a second deriver 66 which derives red cell index targets and ranges for the application of the Westgard Rules.

The components of the automated calibration system which are described above may be realized by using a microprocessor, microcontroller or CPU 24, discrete electrical components or circuits, or software.

Automated diagnostic analyzers, such as hematology analyzers, can have their stability improved and bias reduced in accordance with the system and method of the present invention utilizing hematology fundamentals for red cell indices with species specific targets (for veterinary applications, in particular), a gradient descent algorithm, and fuzzy logic. A simple PCV (packed cell volume) comparison with HCT can verify proper adjustments to the analyzer's settings and ensure accuracy with or without utilizing fixed cell controls or splitting samples with a reference laboratory. The system and method of the present invention are quite useful with veterinary hematology analyzers and in veterinary offices, where control fluid costs are prohibitive to their regular use, and many are based on human fixed cells requiring different algorithms than used with patient samples.

Using patient-based results to monitor and control system performance is effective since species-specific variations can be identified in the manner used to generate results. While a single patient-result will not provide ample power to make decisions and take actions regarding system performance, aggregated patient-based results provide increasing analytical power. As the number of samples for analysis increases, so does the analytical power. As the length of time and number of runs for analysis increases, so does the time before actions can be taken. Due to the desire to have high analytical power and quick response time, it is critical to balance the sample size with the required power for taking actions.

The fundamental assumption that must be met in order for the batches to be representative of the instrument response and not patient results is that samples included in a batch must be from a random population of patients. As long as the data set is random, samples are not repeated, and large groups (more than 30% of two consecutive batches worth of runs) of patient results with similar abnormal response conditions are not run in sequence, the statistics will be sufficient to generate batches that are representative of instrument response. These batches can then be used to adjust the system response for accuracy.

There are many benefits of utilizing batches to summarize patient samples into a control chart. Bull's logic provides a means to reduce the impact of single sample variations on batch results. Furthermore, utilizing this analysis for red cell parameters (RBC, HCT, HGB, MCV, MCH and MCHC) has additional benefits, since several parameters including MCV, MCH and MCHC have tight normal variations within species that can provide additional information with respect to result accuracy. Some concerns have been raised since the adjustment analysis references "targets" based on a central reference interval value for the particular parameter. These concerns are generally related to specialty practices running multiple sick patients, but this can be mitigated since there are few clinical conditions that drive significant variation in MCV, MCH, and MCHC for a population of patients. A practitioner can identify that the system is not functioning correctly when the population MCHC is biased near 37 or 29; however, this analysis will utilize optimizing logic to find and correct biases before they are at this level of bias.

Consideration for species-specific results also provides value in this analysis. Consider a system with a fixed-cell control material based on human cells. The instrument will run the control sequence and algorithm, commonly with an MCV>80 fL. The system may be functioning correctly for this material, but there may be species-specific biases seen since canine MCV is nominally around 70 fL and feline will be <50 fL. Depending on the technology, algorithm, and performance across this large range, there may be species-specific adjustments required. As the hematology system ages, the response may not be linear with the control material and application of weighted moving average analysis may be required to assure accurate MCV values for different species.

The described approach provides a means to ensure that the analysis system is functioning correctly, and provide feedback control to maintain accurate performance. Logic must be included to ensure that pre-analytical errors do not drive adjustments to the analyzer to compensate for bad preparation. For example, consistent pre-analytical errors causing in vitro hemolysis will result in high MCHC values, but the instrument should not be adjusted since it will cause accurate measurements to be biased due to the adjustment. Other pre-analytical concerns, such as the presence of significant lipemia, could also affect automated analysis. Logic can be put in place to block against some of these known conditions, but it is up to the practitioner to ensure that proper laboratory practices are employed to help ensure correct automated analyses.

Additional benefits are realized by ensuring performance with patient samples utilizing the method of the present invention in conjunction with control fluids, since this provides another reference to add statistical power to the analysis. The application of this method of weighted moving averages analysis for other hematology parameters is possible. In addition, these methods may be optimized for chemistry analyzer performance and have potential value. The analytical power of the analysis is derived by the knowledge that mean values converge quickly, even in systems with large normal variation from the instrument and/or the sample population. The method of the present invention described herein has been tested with automated veterinary hematology analyzers for selected parameters, but it may be directly generalized to veterinary chemistry. In addition, human hematology and chemistry systems could utilize the method of the present invention above and beyond the implementation of Bull's Algorithm to optimize use of controls and automate feedback control.

The system and method of the present invention will make the adjustments, as required, to the calculations performed by the analyzer, in real time, without the need for the clinician to make adjustments to the analyzer manually based on the clinician's interpretation of graphs and other data presented on a display of the analyzer, thereby minimizing or eliminating errors in the clinician's analysis or his possibly overcorrecting a perceived instrumentation bias.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An automated method for calibrating in real time a diagnostic analyzer, which comprises the steps of:
    receiving diagnostic results of patient samples calculated by the analyzer using the pre-set parameters of the analyzer;
    applying a weighted moving averages algorithm to the patient sample diagnostic results to obtain weighted averaged diagnostic results;
    applying control chart rules to the weighted averaged diagnostic results, and creating from the control chart rules limits or ranges which are used to test the extent to which the weighted averaged diagnostic results reside within such limits or ranges;
    comparing the weighted averaged diagnostic results with such control chart rule limits or ranges;
    if the weighted averaged diagnostic results fall within the control chart rule limits or ranges, then not applying a multiplying factor to the patient sample diagnostic results calculated by the analyzer using its pre-set parameters;
    if the weighted averaged diagnostic results fall outside of the control chart rule limits or ranges during such a comparison, then applying fuzzy logic and a gradient descent algorithm to the weighted averaged diagnostic results to obtain adjusted diagnostic results of the patient samples which are now within the acceptable limits or ranges of the control chart rules;
    reading out or displaying such adjusted diagnostic results by the analyzer;
    deriving one or more multiplying factors from the application of the fuzzy logic and the gradient descent algorithm to the weighted averaged diagnostic results; and
    modifying the calculations performed by the analyzer with its pre-set parameters by the multiplying factor (or factors) to correct the results of the analyzer calculations without the need to change the analyzer's pre-set parameters by automatically feeding back to the analyzer the derived one or more multiplying factors and applying the derived one or more multiplying factors to the calculations of the patient sample diagnostic results read out or displayed by the analyzer.

2. An automated method for calibrating in real time a diagnostic analyzer as defined by claim 1, wherein the weighted moving averages algorithm applied to the patient samples is Bull's algorithm.

3. An automated method for calibrating in real time a diagnostic analyzer as defined by claim 1, wherein the control chart rules are Westgard Rules, and which further comprises the step of:
    deriving red cell index targets and ranges for the application of the Westgard Rules.

4. An automated method for calibrating in real time a diagnostic analyzer as defined by claim 3, wherein the red cell targets and ranges are derived for certain selected species of animals.

5. An automated method for calibrating in real time a diagnostic analyzer as defined by claim 1, wherein the diagnostic analyzer is selected from the group consisting of hematology analyzers and chemistry analyzers.

6. An automated method for calibrating in real time a diagnostic analyzer as defined by claim 1, wherein the diagnostic analyzer is a hematology analyzer.

7. An automated method for calibrating in real time a diagnostic analyzer as defined by claim 1, wherein the step of applying fuzzy logic and a gradient descent algorithm to the weighted averaged diagnostic results to obtain adjusted diagnostic results if the weighted averaged diagnostic results fall outside of the control chart rule limits or ranges further includes the step of optimizing the adjusted diagnostic results obtained by repeatedly applying as necessary fuzzy logic and the gradient descent algorithm to the weighted averaged diagnostic results.

8. An automated method for calibrating in real time a diagnostic analyzer as defined by claim 1, wherein the gradient descent algorithm applied to the weighted averaged diagnostic results is a 2-d gradient descent algorithm.

9. An automated system for calibrating in real time a diagnostic analyzer, the diagnostic analyzer performing calculations on patient diagnostic samples using pre-set parameters, which comprises:
    one or more memories in which are stored a weighted moving averages algorithm, control chart rules, fuzzy logic, a gradient descent algorithm and a multiplying factor; and a microprocessor operatively coupled to the one or more memories, the microprocessor carrying out the operations of the weighted moving averages algorithm, the control chart rules, the fuzzy logic and the gradient descent algorithm to patient data and making comparisons to determine if weighted averaged diagnostic results are within control chart rule limits or ranges, and deriving the multiplying factor to be applied to the analyzer's pre-set parameters, the derived multiplying factor being automatically fed back to the analyzer and used to modify the calculations performed by the analyzer on the patient diagnostic samples.

10. An automated system for calibrating in real time a diagnostic analyzer, as defined by claim 9, wherein the diagnostic analyzer is selected from the group consisting of hematology analyzers and chemistry analyzers.

11. An automated system for calibrating in real time a diagnostic analyzer, as defined by claim 9, wherein the diagnostic analyzer is a hematology analyzer.

12. An automated system for calibrating in real time a diagnostic analyzer, the diagnostic analyzer performing calculations on patient diagnostic samples using pre-set parameters, which comprises:
   means for receiving diagnostic results of patient samples calculated by the analyzer using the pre-set parameters of the analyzer;
   means for applying a weighted moving averages algorithm to the patient sample diagnostic results to obtain weighted averaged diagnostic results;
   means for applying control chart rules to the weighted averaged diagnostic results, and creating from the control chart rules limits or ranges which are used to test the extent to which the weighted averaged diagnostic results reside within such limits or ranges;
   means for selectively applying fuzzy logic and a gradient descent algorithm to the weighted averaged diagnostic results;
   means for comparing the weighted averaged diagnostic results with such control chart rule limits or ranges, wherein if the weighted averaged diagnostic results fall within the control chart rule limits or ranges, then a multiplying factor is not applied to the patient sample diagnostic results calculated by the analyzer using its pre-set parameters, and wherein if the weighted averaged diagnostic results fall outside of the control chart rule limits or ranges during such a comparison, then the means for applying fuzzy logic and a gradient descent algorithm apply fuzzy logic and the gradient descent algorithm to the weighted averaged diagnostic results to obtain adjusted diagnostic results of the patient samples which are now within the acceptable limits or ranges of the control chart rules;
   means for reading out or displaying such adjusted diagnostic results by the analyzer;
   means for deriving one or more multiplying factors from the application of the fuzzy logic and the gradient descent algorithm to the weighted averaged diagnostic results; and
   means for modifying the calculations performed by the analyzer with its pre-set parameters by the multiplying factor (or factors) to correct the results of the analyzer calculations without the need to change the analyzer's pre-set parameters by automatically feeding back to the analyzer the derived one or more multiplying factors and applying the derived one or more multiplying factors to the calculations of the patient sample diagnostic results read out or displayed by the analyzer.

13. An automated system for calibrating in real time a diagnostic analyzer as defined by claim 12, wherein the means for applying control chart rules apply Westgard Rules to the patient sample diagnostic results to obtain the weighted averaged diagnostic results;
   and wherein the automated system further comprises means for deriving red cell index targets and ranges for the application of the Westgard Rules.

14. An automated system for calibrating in real time a diagnostic analyzer as defined by claim 12, wherein the means for selectively applying fuzzy logic and a gradient descent algorithm to the weighted averaged diagnostic results selectively applies a 2-d gradient descent algorithm to the weighted averaged diagnostic results.

15. An automated system for calibrating in real time a diagnostic analyzer, the diagnostic analyzer performing calculations on patient diagnostic samples using pre-set parameters, which comprises:
   a receiver which receives diagnostic results of patient samples calculated by the analyzer using the pre-set parameters of the analyzer;
   a first applier which applies a weighted moving averages algorithm to the patient sample diagnostic results to obtain weighted averaged diagnostic results;
   a second applier which applies control chart rules to the weighted averaged diagnostic results, and which creates from the control chart rules limits or ranges which are used to test the extent to which the weighted averaged diagnostic results reside within such limits or ranges;
   a third applier which selectively applies fuzzy logic and a gradient descent algorithm to the weighted averaged diagnostic results;
   a comparator which compares the weighted averaged diagnostic results with such control chart rule limits or ranges, wherein if the weighted averaged diagnostic results fall within the control chart rule limits or ranges, then a multiplying factor is not applied to the patient sample diagnostic results calculated by the analyzer using its pre-set parameters, and wherein if the weighted averaged diagnostic results fall outside of the control chart rule limits or ranges during such a comparison, then the third applier applies the fuzzy logic and the gradient descent algorithm to the weighted averaged diagnostic results to obtain adjusted diagnostic results of the patient samples which are now within the acceptable limits or ranges of the control chart rules;
   a reader or displayer which reads out or displays the adjusted diagnostic results by the analyzer;
   a first deriver which derives one or more multiplying factors from the application of the fuzzy logic and the gradient descent algorithm to the weighted averaged diagnostic results; and
   a modifier which modifies the calculations performed by the analyzer with its pre-set parameters by the multiplying factor (or factors) to correct the results of the analyzer calculations without the need to change the analyzer's pre-set parameters by automatically feeding back to the analyzer the derived one or more multiplying factors and applying the derived one or more multiplying factors to the calculations of the patient sample diagnostic results read out or displayed by the analyzer.

16. An automated system for calibrating in real time a diagnostic analyzer as defined by claim 15, wherein the third applier which applies Westgard Rules to the patient sample diagnostic results to obtain the weighted averaged diagnostic results;

and wherein the automated system further comprises a second deriver which derives red cell index targets and ranges for the application of the Westgard Rules.

17. An automated system for calibrating in real time a diagnostic analyzer as defined by claim 15, wherein the third applier which selectively applies fuzzy logic and a gradient descent algorithm to the weighted averaged diagnostic results selectively applies a 2-d gradient descent algorithm to the weighted averaged diagnostic results.

* * * * *